US008431355B2

(12) United States Patent
Ronin et al.

(10) Patent No.: US 8,431,355 B2
(45) Date of Patent: Apr. 30, 2013

(54) PROCESS FOR SCREENING GLYCOFORM-SPECIFIC ANTIBODIES

(75) Inventors: Catherine Ronin, Sausset-les-Pins (FR); Sandrine Donadio, Marseilles (FR)

(73) Assignee: Universite de Provence Aix-Marseille 1, Marseilles (FR)

( * ) Notice: Subject to any disclaimer, the term of this patent is extended or adjusted under 35 U.S.C. 154(b) by 1086 days.

(21) Appl. No.: 10/588,220

(22) PCT Filed: Feb. 4, 2005

(86) PCT No.: PCT/EP2005/001160
§ 371 (c)(1), (2), (4) Date: Apr. 17, 2008

(87) PCT Pub. No.: WO2005/076013
PCT Pub. Date: Aug. 18, 2005

(65) Prior Publication Data
US 2008/0199892 A1 Aug. 21, 2008

(30) Foreign Application Priority Data
Feb. 4, 2004 (EP) .................................... 04290290

(51) Int. Cl.
| | |
|---|---|
| G01N 33/76 | (2006.01) |
| G01N 33/53 | (2006.01) |
| C07K 16/26 | (2006.01) |
| C07K 14/59 | (2006.01) |
| C12Q 1/48 | (2006.01) |
| C12N 5/16 | (2006.01) |

(52) U.S. Cl.
USPC ............ 435/7.94; 435/7.92; 435/7.1; 435/14; 435/15; 435/68.1; 435/336; 435/971; 436/507; 530/388.24

(58) Field of Classification Search ........................ None
See application file for complete search history.

(56) References Cited

U.S. PATENT DOCUMENTS
5,976,876 A  11/1999 Canfield et al.

FOREIGN PATENT DOCUMENTS
| | | |
|---|---|---|
| EP | 1 143 250 A2 | 10/2001 |
| WO | 99/39202 | 8/1999 |
| WO | 99/66956 | 12/1999 |

OTHER PUBLICATIONS

Papandreou et al, J Clinical Endocrinology and Metabolism 77(2): 393-398, 1999.*
International Search Report of PCT/EP2005/001160, mailed Oct. 18, 2005.
Zanusso et al., "Prion Protein Expression in Difference Species: Analysis With a Panel of New mAbs", Proceedings of the National Academy of Sciences of USA, vol. 95, Jul. 21, 1998, pp. 8812-8816, XP002924868.
Zerfaoui et al., "Glycosylation is the structural basis for changes in polymorphism and immunoreactivity of pituitary glycoprotein hormones", European Journal of Clinical Chemistry and Clinical Biochemistry, vol. 34, No. 9, 1996, pp. 749-753, XP009033136.
Oliver et al., "Do immunoassays differentially detect different acidity glycoforms of FSH?", Clinical Endocrinology, vol. 51, No. 6, Dec. 1999, pp. 681-686, XP001182256.
Dias, "Is there any physiological role for gonadotrophin oligosaccharide heterogeneity in humans? II. A biochemical point of view", Human Reproduction, vol. 16, No. 5, May 2001, pp. 825-830, XP002287046.
Szkudlinski et al., "Thyroid-stimulating hormone and thyroid-stimulating hormone receptor structure-function relationships", Physiological Reviews, vol. 82, No. 2, Apr. 2002, pp. 473-502, XP002287047.
Lundy et al., "An antibody-lectin sandwich assay for quantifying protein glycoforms", Molecular Biotechnology, vol. 12, No. 2, Sep. 1999, pp. 203-206, XP009033133.
Canonne et al.,"Biological and Immunochemical Characterization of Recombinant Human Thyrotrophin", Glycobiology, vol. 5, No. 5, 1995, pp. 473-481, vol. 5, No. 5, 1995, pp. 473-481, XP09033167.
Papandreou et al., "Carbohydrate-Dependent Epitope Mapping of Human Thyrotropin", Molecular and Cellular Endocrinology, vol. 73, No. 1, 1990, pp. 15-26, XP001188294.
Legaigneur et al., "Exploring the acceptor substrate recognition of the human beta-Galactoside alpha2, 6-sialyltransferase", Journal of Biological Chemistry, vol. 276, No. 24, Jun. 15, 2001, pp. 21608-21617, XP002326446.
Szkudlinski et al., "Human Thyroid-Stimulating Hormone: Structure-Function Analysis", Methods: A Companion to Methods in Enzymology, vol. 21, No. 1, May 2000, pp. 67-81, XP004466911.
Thotakura et al., "Structure-Function Studies of Oligosaccharides of Recombinant Human Thyrotrophin by Sequential Deglycosylation and Resialylation", Glycobiology, vol. 4, No. 4, 1994, pp. 525-533, XP009047051.
Schaaf et al., "Glycosylation variants of human TSH selectively activate signal transduction pathways", Molecular and Cellular Endocrinology, vol. 132, No. 1-2, 1997, pp. 185-194, XP002342993.
Szkudlinski et al., "Purification and characterization of recombinant human thyrotropin (TSH) isoforms produced by Chinese hamster ovary cells: The role of sialylation and sulfaction in TSH bioactivity", Endocrinology, vol. 133, No. 4, 1993, pp. 1490-1503, XP002342828.

(Continued)

*Primary Examiner* — Phuong Huynh
(74) *Attorney, Agent, or Firm* — Nixon & Vanderhye P.C.

(57) ABSTRACT

The present invention relates to the use of the assessment of the binding between—antibodies elicited against a first glycoprotein, and—at least one glycoform of a second glycoprotein, said second glycoprotein being itself a glycoform of the first protein, wherein said glycoform of the second glycoprotein is selected from a group of glycoforms of the second glycoprotein, each glycoform of said group corresponding to a determined glycosylation state defined by a determined sialylation state, and/or a determined branching state, and/or a determined fucosylation state, provided that said glycosylation state is not uniquely defined by a substantially unsialylated state, for the screening of glycoform specific antibodies directed against a given glycoform of the second glycoprotein.

16 Claims, 22 Drawing Sheets

OTHER PUBLICATIONS

Kashiwai et al., "Immunological and Biological Characteristics of Recombinant Human Thyrotropin", Journal of Immunological Methods, vol. 143, No. 1, 1991, pp. 25-30, XP002342994.

Nemansky et al., "Enzymic remodeling of the N- and O-linked carbohydrate chains of human chorionic gonadotropin: Effects on biological activity and receptor binding", European Journal of Biochemistry, vol. 227, No. 3, 1995, pp. 880-888, XP002342995.

Thotakura et al. "Biological Activity and Metabolic Clearance of a Recombinant Human Thyrotropin Produced in Chinese Hamster Ovary Cells" Endocrinology. Jan. 1991;128(1):341-8 (Abstract).

Szkudlinski et al. "Subunit-specific functions of N-linked oligosaccharides in human thyrotropin: Role of terminal residues of $\alpha$- and $\beta$-subunit oligosaccharides in metabolic clearance and bioactivity" PNAS. Sep. 1995; vol. 92 :9062-9066.

* cited by examiner

PROCESS FOR SCREENING GLYCOFORM-SPECIFIC ANTIBODIES

This application is the US national phase of international application PCT/EP2005/001160, filed 4 Feb. 2005, which designated the U.S. and claims priority of EP 04 290 290.8, filed 4 Feb. 2004, the entire contents of each of which are hereby incorporated by reference.

The present invention relates to a process for screening glycoform-specific antibodies. The present invention also relates to a process for optimizing the recognition of specific glycoforms of a given glycoprotein.

There is currently a growing demand for measurement systems in which antibodies discriminate glycoproteins having a particular glycosylation pattern (i.e. discriminate specific glycoforms of a given glycoprotein). Such antibodies are particularly helpful for immunological assays intended for detecting and measuring the concentration of particular glycoforms of a given glycoprotein in body tissues and/or fluids.

For instance, the concentration, glycosylation and/or tissular source of glycoprotein hormones, such as TSH, LH or FSH, may be indicative of certain pathologies (Spencer, C. A. et al., 1995; Spencer, C. A., and Demers, L. M., 2003).

However, several obstacles preclude the obtaining of such antibodies, the most important of which concerns the glycoprotein to be used to screen and/or to elicit the production of antibodies.

It is difficult to obtain glycoproteins with a desired glycosylation pattern, especially with a human-type glycosylation pattern, reliably and in large amounts. Thus, human or animal sources of glycoproteins, provide for very scarce amounts of protein. Moreover, the glycosylation pattern of the glycoproteins originating from animals is relatively different from that of human origin.

Recombinant glycoproteins are not an interesting alternative, in that the cell lines used for producing recombinant glycoproteins are mostly of animal origin. Therefore, these cell lines lead to the obtaining of a glycosylation pattern which markedly differ from the human-type glycosylation pattern. Besides, human cell lines can not produce all the various tissue-specific glycosylated glycoproteins.

Accordingly, research is currently being conducted to genetically design new cellular lines so as to produce glycoproteins carrying particular human type glycosylation patterns. Yet these lines are still not suited for protein production in large quantities and the cell line system is not sufficiently versatile to reproduce the whole array of human glycosylation types.

In another instance, the immunoreactivity of desialylated recombinant TSH produced in CHO cells was studied (Zerfaoui, M., and Ronin, C., 1996). However, the interest of using this single modification to screen glycoform-specific antibodies is dismal because most natural glycoproteins, especially those circulating in blood, are sialylated to a certain extent.

Besides, current TSH immunometric assays have been long established to represent the most sensitive and reliable approach for thyroid function testing. However, several comparative studies revealed significant inter- and intra-immunoprocedures variations in TSH measurements, possibly resulting in mis- or undiagnosed patients and consequently misfit treatments. When recombinant TSH (recTSH) was first produced in CHO cells (Price, A., et al., 2001), this compound was felt to be a putative new candidate to replace the routinely used $2^{nd}$ International Reference Preparation (IRP) of pituitary-extracted TSH. In 1999, the World Health Organization ordered a worldwide survey to validate the recombinant compound as a new Reference Material. Measurements of a recTSH preparation (94/674) were performed in 38 different immunoprocedures by means of different formats i.e. RIA, IRMA, ELISA, IFMA, and/or ICLMA and standardized against the $2^{nd}$ IRP pitTSH (80/558). The study revealed a significant variability from 5.51 mIU (3.95-7.67 mIU) per ampoule by RIA to 7.15 mIU (6.7-7.63 mIU) per ampoule by IFMA (Rafferty, B., et al., 1999). The potential use of this compound as new calibrant in TSH measurements was not documented further.

Thus, the present invention aims at:
 providing a new process for screening glycoform-specific antibodies;
 using the screened antibodies for the detection of a given glycoprotein;
 providing a process for isolating specific glycoforms of a given glycoprotein, said glycoforms being used:
  to screen glycoform-specific epitopes,
  to replace said glycoprotein to calibrate glycoform-specific immunoassays, or
  to elicit glycoform-specific antibodies.

The present invention relates to the use of the assessment of the binding between
 antibodies elicited against a first glycoprotein, and
 at least one glycoform of a second glycoprotein, said second glycoprotein being itself a glycoform of the first protein,
wherein said glycoform of the second glycoprotein is selected from a group of glycoforms of the second glycoprotein, each glycoform of said group corresponding to a determined glycosylation state defined by a determined sialylation state, and/or a determined branching state, and/or a determined fucosylation state, provided that said glycosylation state is not uniquely defined by a substantially unsialylated state,
for the screening of glycoform specific antibodies directed against a given glycoform of the second glycoprotein.

Most glycoproteins can be found under several forms which vary from each other by their respective glycan content, their respective protein sequence being essentially similar, i.e. the amino acid sequence similarity of each glycoprotein as compared to each other being greater than 90%, preferably greater than 95%, provided that both glycoproteins display the same biological properties; those forms are called glycoforms of a given glycoprotein.

The expression "antibodies elicited against a first glycoprotein" means that said antibodies are obtained after immunization of an animal by said first glycoprotein.

Advantageously those antibodies are monoclonal antibodies.

The glycosylation state of a given glycoprotein corresponds to the number of glycan chains carried by said glycoprotein and to the respective structures of those chains.

As a general rule a given glycoform can be characterized by a determined glycosylation state. However, it is worth noting that due to the remarkable diversity of the various protein glycosylation processes in cells, a given glycoform does not correspond to a unique glycosylation pattern but to a set of several closely related glycosylation patterns which can be accounted for by their average glycan structure. This average glycan structure will be herein understood to correspond to said glycosylation state.

The sialylation state corresponds to the number of sialyl groups which are carried by a given glycoprotein. In human glycoproteins, sialic acid most often corresponds to N-acetylneuraminic acid (NeuAc).

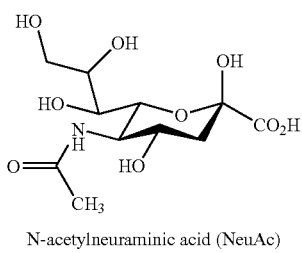

N-acetylneuraminic acid (NeuAc)

The expression "substantially unsialylated state" refers to a glycosylation pattern essentially lacking sialyl groups.

A glycosylation state is said to be "not uniquely defined by a substantially unsialylated state" if it is either not unsialylated or if its unsialylation is associated with other modification of the glycosylation state.

A glycoform, the glycosylation state of which is uniquely defined by a substantially unsialylated state, is of no relevance in the frame of the present invention since this feature is not a natural glycosylation feature, in particular in human circulation.

The fucosylation state corresponds to the number of fucosyl group which are carried by a given glycoprotein. In human glycoproteins, fucose corresponds to L-deoxygalactose.

The branching state corresponds to the number of β1,2/4/6 linked N-acetylglucosamine residues established with either of the branched mannose residue of the invariant pentasaccharide of N-linked glycans.

By way of illustration the structure of a typical N-linked glycan chain is represented in FIG. 1A.

The glycan chain composition, especially the estimation of NeuAc, of fucose and of the degree of branching, can be assessed by acid hydrolysis of the glycoprotein, followed by derivatization and gas chromatography (Methods on Glycoconjugates: a laboratory manual. Ed: André Verbert, 1995). These data indicate the average composition per glycan chain (i.e. for 3 mannose residues).

A detailed glycan structure is obtained after releasing the glycan chains by endoglycosidase treatment and isolating each glycan chain by HPLC, following or not chemical derivatization by a fluorophore group. The molecular size of each species/peak is then resolved by mass spectrometry and its carbohydrate sequence is assessed by glycosidase sequential removal and further analysis of the shift in molecular weight using the same technique.

The present invention also relates to a process for screening glycoform specific antibodies among antibodies elicited against a first glycoprotein, comprising a step of determination of the binding between
  antibodies elicited against a first glycoprotein, and
  at least one glycoform of a second glycoprotein, said second glycoprotein being itself a glycoform of the first protein,
wherein said glycoform of the second glycoprotein is selected from a group of glycoforms of the second glycoprotein, each glycoform of said group corresponding to a determined glycosylation state defined by a determined sialylation state, and/or a determined branching state, and/or a determined fucosylation state, provided that said glycosylation state is not uniquely defined by a substantially unsialylated state
to recover antibodies liable to bind to at least one given glycoform of the second glycoprotein.

According to a particular embodiment, the glycosylation state of the glycoform of the second glycoprotein presents at least one of the following criteria:

it is essentially more sialylated than said second glycoprotein, or
  it is essentially less sialylated than said second glycoprotein, or
  it is essentially more branched than said second glycoprotein, or
  it is essentially less branched than said second glycoprotein, or
  it is essentially more fucosylated than said second glycoprotein, or
  it is essentially less fucosylated than said second glycoprotein.

The expression "more sialylated" means that the glycan chains of said glycoform contain on average more sialyl groups than the glycan chains of the second glycoprotein do.

The expression "less sialylated" means that the glycan chains of said glycoform contain on average less sialyl groups than the glycan chains of the second glycoprotein do.

The expression "more branched" means that the glycan chains of said glycoform are on average more branched than the glycan chains of the second glycoprotein are.

The expression "less fucosylated" means that the glycan chains of said glycoform are on average less branched than the glycan chains of the second glycoprotein are.

The expression "more fucosylated" means that the glycan chains of said glycoform contain on average more fucosyl groups than the glycan chains of the second glycoprotein do.

The expression "less fucosylated" means that the glycan chains of said glycoform contain on average less fucosyl groups than the glycan chains of the second glycoprotein do.

These glycosylation states can be determined following the above described procedure.

Glycan heterogeneity is known to affect pharmacokinetics of glycoproteins, especially those circulating in blood depending on their sialic acid content. Glycosylation is often controlling biological properties of glycoproteins, such as receptor activation, pharmacokinetics of glycoprotein hormones (TSH, LH, FSH and hCG) and also physicochemical/structural properties, such as solubility, isoelectric point, thermal stability and resistance to proteolytic degradation. Except for sialic acid, these modifications cannot be attributed to a single monosaccharide, but often results from a steric contribution of the whole glycan chain.

According to another particular embodiment, the binding between at least one of the antibodies elicited against the first glycoprotein and each of the glycoforms of the second glycoprotein which are respectively:
  essentially more sialylated than said second glycoprotein,
  essentially less sialylated than said second glycoprotein,
  essentially more branched than said second glycoprotein,
  essentially less branched than said second glycoprotein,
  essentially more fucosylated than said second glycoprotein, and
  essentially less fucosylated than said second glycoprotein,
is determined.

According to another particular embodiment, the glycosylation state of the glycoform of the second glycoprotein presents at least two of the following criteria:
  it is essentially more sialylated or less sialylated than said second glycoprotein,
  it is essentially more branched or less branched than said second glycoprotein,
  it is essentially more fucosylated or less fucosylated than said second glycoprotein.

These modifications act as a combinatory code to generate a remarkable microheterogeneity onto the polypeptide backbone of the protein, affecting both its physicochemical and biological properties. In the case of glycoprotein hormones, inner glycosylation controls subunit association, immunologically and biologically active conformation, while the signal sulphate/sialic acid governs pulsatility and metabolic clearance because it is under the control of the endocrine hypothalamo-pituitary axis.

"Inner glycosylation" typically refers to the invariant pentasaccharide attached to the polypeptide by a N-glycosidic bond. It is known that fucosylation of this core enhances its hydrophobicity and rigidity and, as a result, may alter the conformation of any peptide area covered by the whole glycan.

According to another particular embodiment, the glycosylation state of the glycoform of the second glycoprotein presents one of the following criteria:
  it is essentially more sialylated and more fucosylated than said second glycoprotein, or
  it is essentially more sialylated and less fucosylated than said second glycoprotein, or
  it is essentially more sialylated and more branched than said second glycoprotein, or
  it is essentially more sialylated and less branched than said second glycoprotein, or
  it is essentially less sialylated and more fucosylated than said second glycoprotein, or
  it is essentially less sialylated and less fucosylated than said second glycoprotein, or
  it is essentially less sialylated and more branched than said second glycoprotein, or
  it is essentially less sialylated and less branched than said second glycoprotein, or
  it is essentially more branched and more fucosylated than said second glycoprotein, or
  it is essentially more branched and less fucosylated than said second glycoprotein, or
  it is essentially less branched and more fucosylated than said second glycoprotein, or
  it is essentially less branched and less fucosylated than said second glycoprotein.

According to another particular embodiment, the glycosylation state of the glycoform of the second glycoprotein presents three of the following criteria:
  it is essentially more sialylated or less sialylated than said second glycoprotein,
  it is essentially more branched or less branched than said second glycoprotein,
  it is essentially more fucosylated or less fucosylated than said second glycoprotein.

These modifications generate a remarkable microheterogeneity onto the polypeptide backbone of the protein, affecting both its physicochemical and biological properties during biosynthesis, intracellular migration, secretion and further action at the target tissue. In the case of glycoprotein hormones, this heterogeneity at different levels also controls subunit association, activation of the target receptor, pulsatility and metabolic clearance because it is under the control of the endocrine hypothalamo-pituitary axis.

According to another particular embodiment, the glycosylation state of the glycoform of the second glycoprotein presents one of the following criteria:
  it is essentially more sialylated, more branched and more fucosylated than said second glycoprotein,
  it is essentially more sialylated, more branched and less fucosylated than said second glycoprotein,
  it is essentially more sialylated, less branched and more fucosylated than said second glycoprotein,
  it is essentially more sialylated, less branched and less fucosylated than said second glycoprotein,
  it is essentially less sialylated, more branched and more fucosylated than said second glycoprotein,
  it is essentially less sialylated, more branched and less fucosylated than said second glycoprotein,
  it is essentially less sialylated, less branched and more fucosylated than said second glycoprotein,
  it is essentially less sialylated, less branched and less fucosylated than said second glycoprotein.

According to a preferred embodiment, the antibodies elicited against the first glycoprotein bind to the second glycoprotein with an affinity equal to or higher than the binding affinity of said antibodies to the first glycoprotein.

The measure of the affinity of an antibody for a given glycoprotein can be done according to Benkirane, M. M., et al., 1987.

According to another preferred embodiment, at least one lectin fractionation of the second glycoprotein is performed to obtain a glycoform of the second glycoprotein of a determined glycosylation state.

By "lectin" is meant a sugar-binding protein of non-immune origin, which agglutinates cells and/or recognize glycoconjugates. Lectins are classified according to the monosaccharide which inhibits the interaction between the lectin and the targeted glycan or which allows the specific elution of a bound glycan from an immobilized lectin column. The expression "lectin fractionation" means that glycoforms are separated according to their binding affinity for a given lectin insolubilized on a matrix and used as a chromatography column.

Certain lectins have a specific affinity towards a given monosaccharide, like mannose/glucose, fucose, galactose/N-acetylgalactosamine, N-acetyl-glucosamine or N-acetyl-neuraminic acid.

Advantageously sugar-specific lectin fractionation enables to separate glycoproteins according to their content in said sugar.

According to another preferred embodiment, the lectin is selected from the group comprising mannose-specific lectins, such as the ConA or Lentil lectins, fucose-specific lectins, such as the *Ulex* lectin, gactose-specific lectins, such as ricin, or sialic acid-specific lectins, such as limulin or the *Sambucus nigra* lectin.

Those lectins are commercially available and well known to the man skilled in the art.

According to another preferred embodiment, at least one enzymatic modification of the second glycoprotein is performed to obtain a glycoform of the second glycoprotein of a determined glycosylation state.

By enzymatic modification is meant that one or more carbohydrate groups are added, removed or modified in a given glycoprotein.

According to another preferred embodiment, the enzymatic modification is carried out by an enzyme selected from the group comprising a glycosidase, in particular a neuraminidase or a fucosidase, or a glycosyltransferase, in particular a sialyl transferase or a fucosyl transferase.

A neuraminidase selectively removes sialic acid from glycoproteins.

A sialyl transferase specifically adds sialyl groups onto a glycoprotein.

A fucosidase selectively removes fucose from glycoproteins.

A fucosyl transferase specifically adds fucosyl groups onto a glycoprotein.

According to a particularly preferred embodiment, a glycoform of the second glycoprotein of a determined glycosylation state is obtained by a combination of at least one enzymatic modification of the second glycoprotein and/or of at least one lectin fractionation.

According to another preferred embodiment, a less sialylated glycoform of the second glycoprotein as compared to the second glycoprotein is obtained by neuraminidase treatment of said second glycoprotein.

According to another preferred embodiment, a more sialylated glycoform of the second glycoprotein as compared to the second glycoprotein is obtained by sialyltransferase treatment of said second glycoprotein or by neuraminidase treatment followed by sialyltransferase treatment of said second glycoprotein.

According to a particularly preferred embodiment, the sialyltransferase is a α-2,6 sialyltransferase, in particular a ST6GalI sialyltransferase, more particularly a N-terminal shortened ST6GalI sialyltransferase deleted of at most its first 99 residues, such as represented by SEQ ID NO: 1.

Such N-terminal shortened ST6GalI sialyltransferases are notably described in Legaigneur, P., et al. (2001). Preferred shortened human ST6GalI sialyltransferase are Δ1-35 ST6GalI and Δ1-89 ST6GalI (SEQ ID NO: 1) which respectively lack the 35 and 89 first N-terminal residues with respect to the wild type human ST6GalI.

According to a preferred embodiment, a less fucosylated glycoform of the second glycoprotein as compared to the second glycoprotein is obtained by lentil fractionation of the second glycoprotein by collecting the fraction which does not bind to lentil and a more fucosylated glycoform of the second glycoprotein as compared to the second glycoprotein is obtained by collecting the fraction which binds to lentil.

According to yet another preferred embodiment, a ConA fractionation of the second glycoprotein is performed by collecting three fractions, A, B, and C, the binding of which to ConA is such that, C binds to ConA more strongly than B does, and
B binds to ConA more strongly than A does,
the branching state of a given fraction being essentially different from the branching state of the other two fractions.

According to a particular embodiment, in a preliminary step, the antibodies to be screened are classified in pools, each pool being characterized in that two antibodies selected from a same pool can not bind to the same glycoprotein at the same time.

The expression "at the same time" means that both antibodies compete for a similar binding site on said glycoform.

According to another particular embodiment, in a first step, said first step preceding the preliminary step defined above, it is checked that the antibodies elicited against the first glycoprotein bind to the second glycoprotein.

Advantageously, a complete process according to the invention comprises the following steps:

checking that the antibodies elicited against the first glycoprotein bind to the second glycoprotein,
classifying the antibodies to be screened in pools, each pool being characterized in that two antibodies selected from a same pool can not bind to a same glycoform of the second glycoprotein at the same time,
determining the binding between
said antibodies, and
at least one glycoform of the second glycoprotein,
to recover antibodies liable to bind to at least one given glycoform of the second glycoprotein.

According to yet another particular embodiment, the binding of the antibodies to the first glycoprotein, to the second glycoprotein and to the glycoforms of the second glycoproteins is determined by using immunoassays, in particular immunoassay formats using an amplification system for detection, such as an ELISA.

According to a much preferred embodiment, the immunoassay is a sandwich immunoassay, in particular a sandwich ELISA test, comprising the following steps:

fixing a capture antibody, selected from a pool such as defined above, onto a support,
contacting a glycoprotein, corresponding to the first glycoprotein, to the second glycoprotein or to the glycoforms of the second glycoprotein, to said capture antibody, to form, if adequate, a capture antibody-glycoprotein binary complex,
contacting a tracer antibody, selected from a pool such as defined above, provided said pool is different from the one used for the selection of said capture antibody, to said capture antibody-glycoprotein binary complex, to form, if adequate, a capture antibody-glycoprotein-tracer antibody ternary complex,
detecting the tracer antibody for measuring the number of ternary complexes.

The expression "capture antibody" relates to an antibody which is covalently or non-covalently adsorbed onto a support, a so called solid-phase, such as the wall of a microtitration well, so as to form a capture antibody-glycoprotein complex bound to the solid phase.

The expression "tracer antibody" relates to an antibody which can bind said glycoprotein once it is linked to the capture antibody, said tracer antibody being coupled to a detection system. For instance, the tracer antibody can be linked to biotin and be detected using an avidin-enzyme complex, such as alkaline phosphatase or peroxidase, which may be used to activate a fluorogenic and/or a chromogenic substrate, such as p-nitro phenylphosphate, 5 bromo-4-chloro-3indolylphosphate or 1,2 phenyl-enediamine/hydrogen peroxide using an appropriate buffer. Any other enzymatic reaction which is readable with a microtiter spectrofluorometer or spectrophotometer can also be used.

According to another particular embodiment, the first glycoprotein and the second glycoprotein are similar.

The term "similar" means that according to this embodiment the first and the second glycoprotein are the same, that is, they share the same amino acid sequence and the same glycosylation pattern.

According to this particular embodiment, antibodies are elicited against a given glycoprotein, and then the binding of said antibodies with glycoforms of said glycoprotein is determined.

According to yet another particular embodiment, the first glycoprotein and the second glycoprotein originate from different natural tissues and/or fluids.

Tissues and fluids according to the invention notably encompass endocrine tissues, such as the pituitary gland, placenta or endocrine tumors, or fluids such as blood, plasma, serum or urine for instance.

According to still another particular embodiment, the first glycoprotein originates from a natural tissue and the second glycoprotein is a recombinant protein.

Advantageously, the recombinant glycoprotein is produced in mammalian cell lines, in particular Chinese Hamster Ovary (CHO) or human cell lines.

According to a more particular embodiment, the first glycoprotein originates from a natural tissue and the second glycoprotein is a mutated recombinant protein.

By "mutated recombinant protein" is meant that the sequence of second glycoprotein has been modified, with respect to the sequence of the first glycoprotein, by substitution, insertion or deletion of at least one amino acid, provided said second glycoprotein retains hormone-specific immunoreactivity and biological activity.

According to a further particular embodiment, the first glycoprotein is a N-linked glycoprotein, such as TSH, in particular pituitary TSH, LH, FSH, or placental hCG.

Thyroid-Stimulating Hormone (TSH) is a member of the glycoprotein hormone family, which includes pituitary (FSH, LH) and placental (hCG) gonadotropins. These hormones are composed of two different non-covalently linked subunits consisting of a common α-subunit (92 aa in human) and an unique β-subunit (112-118 aa in human) which confers biological and immunological specificity to the hormone heterodimer. TSH possesses two glycans attached to Asn-52 and Asn-78 of the human α-subunit whereas the β-subunit has a single glycan linked to Asn-23.

According to a much preferred embodiment, the first glycoprotein is pituitary TSH and the second glycoprotein is a recombinant TSH.

According to another particular embodiment, the first glycoprotein is pituitary or blood human TSH and the second glycoprotein is a recombinant human TSH, in particular a recombinant human TSH produced in mammalian cells.

In a particularly preferred embodiment the recombinant human TSH is produced by CHO cells.

The present invention further relates to the use of a glycosylation-specific antibody as screened by the above defined process, for the binding or the purification of given glycoforms of the second glycoprotein.

In particular the above glycosylation-specific antibodies can be used for immunodetecting a given glycoform of the second glycoprotein or for immunoassaying the concentration of a given glycoform of the second glycoprotein, in samples, in particular human biological samples.

The above glycosylation-specific antibodies can also be used to purify a given glycoform of the second glycoprotein, for instance by using affinity chromatography, from samples derived either from biological samples or from culture media of cells lines producing recombinant glycoproteins.

According to a preferred embodiment, antibodies R2 and/or OCD1 are used for the binding or the purification of TSH circulating in blood of healthy subjects or of patients suffering from thyroid diseases, such as hypothyroidism, or from non-thyroid diseases coupled to altered levels of TSH, such as endocrine tumors, chronic renal failure or non-thyroid illnesses.

The present invention also relates to a kit for assaying specific glycoforms of the first glycoprotein, characterized in that it comprises:
at least one antibody such as screened according to the above defined process,
at least one glycoprotein calibrant selected from the group comprising the first glycoprotein, the second glycoprotein, and a given glycoform of the second glycoprotein such as defined above.

The expression "glycoprotein calibrant" refers to a glycoprotein which can be used as a standard for the calibration of said kit.

According to a preferred embodiment, the invention relates to a kit as defined above, for assaying TSH in a biological sample, characterized in that it comprises:
at least one antibody selected from the group comprising:
pool I antibodies: B1, B2, S04, S09, R1 and BC27,
pool II antibodies: OCD1 and R2,
pool III antibodies: B3 and S06,
as capture antibody, and at least one antibody selected from the group comprising:
pool I antibodies: B1, B2, S04, S09, R1 and BC27,
pool II antibodies: OCD1 and R2,
pool III antibodies: B3 and S06,
as tracer antibody, provided that the capture antibody and the tracer antibody do not belong to a same pool, and
at least one glycoprotein calibrant which is selected from the group comprising pituitary TSH, substantially unsialylated and/or substantially unfucosylated TSH.

Several immunoassays formats are defined herein depending on the capture antibody/tracer antibody couple used. The choice of a given antibody couple itself depends on the targeted epitopic regions. Three main epitopic region have been defined on TSH in the present invention:
region I, which is recognized by pool I antibodies B1, B2, S04, S09, R1 and BC27,
region II, which is recognized by pool II antibodies OCD1 and R2,
region III, which is recognized by pool III antibodies B3 and S06.

Alternatively region I can be subdivided in regions Ia and Ib, which are respectively recognized by pool Ia antibodies and pool Ib antibodies.

Pool Ia antibodies comprise: S04, B1 and BC27.
Pool Ib antibodies comprise: B2, S09, and R1.

Those antibodies are: OCD1 from Ortho-Clinical Diagnostics, (USA), BC27 commercially available from Beckman-Coulter (USA), R1 and R2 from Roche Diagnostics (G), S04, S06 and S09 commercially available from Seradyn (USA), B1, B2 and B3 from Bayer Diagnostics (G).

More precisely, the panel of monoclonal antibodies is as follows:
OCD1 (ref. 191 29 97) is from Ortho-Clinical Diagnostics, (USA),
BC27 (ref. IM0370) is commercially available from Beckman-Coulter (Immunotech, France),
R1 (ref. 11 367 978) and R2 (ref. 10 767 778) are from Roche Diagnostics (Germany),
S04 (ref MIT0404), S06 (ref. MIT0406) and S09 (ref. MIT0409) are commercially available from Seradyn (USA),
B1, B2 and B3 (ref. 04911359) are from Bayer Diagnostics (Germany).

According to a preferred embodiment, the invention relates to a kit as defined above, for assaying TSH in a biological sample, characterized in that it comprises:
at least one antibody selected from the group comprising BC27, S04, B1, S09, R1, and B2, as capture antibody and at least one antibody selected from the group comprising S06 and B3, as tracer antibody, or
at least one antibody selected from the group comprising S04, B1 and BC27 as capture antibody and at least one antibody selected from the group comprising B2, S09, and R1 as tracer antibody, or
at least one antibody selected from the group comprising S06 and B3 as capture antibody and at least one antibody selected from the group comprising BC27, S04, B1, S09, R1, and B2 as tracer antibody, and
at least one glycoprotein calibrant which is selected from the group comprising pituitary TSH, substantially unsialylated and/or substantially unfucosylated TSH.

This kit is advantageous for assaying TSH from patients with thyroid dysfunction: this immunoassay format is essentially glycosylation independent, that is, antibody binding is not affected by changes in the glycosylation pattern of the protein antigens to be assayed.

In the above defined kit, it is advantageous to use immunoassay formats I/III or preferably III/I, that is to say formats wherein the capture antibody binds to epitopic region I and the tracer antibody binds to epitopic region III, or formats wherein the capture antibody binds to epitopic region III and the tracer antibody binds to epitopic region I.

This kit is advantageous for assaying TSH from healthy subjects or from patients suffering from thyroid diseases coupled to altered levels of TSH in that it is satisfactorily calibrated by a pituitary extract and/or IRP pituitary standard.

According to a preferred embodiment, the invention relates to a kit as defined above, for assaying TSH in a biological sample, characterized in that it comprises:

at least one antibody selected from the group comprising BC27, S04, B1, S09, R1, and B2, as capture antibody, at least one antibody selected from the same group comprising OCD1 and R2 as tracer antibody, and at least one glycoprotein calibrant which is selected from the group comprising recombinant TSH, and a glycoform of recombinant TSH which is substantially more sialylated and/or less fucosylated than said recombinant TSH.

This kit is advantageous for assaying TSH from healthy subjects or from patients suffering from thyroid diseases, such as hypothyroidism, or from non-thyroid diseases coupled to altered levels of TSH; in this kit the immunoassay involved is of format I/II, which is essentially sialylation dependent, that is, antibody binding to glycoforms of a given TSH having an increased sialylation state as compared to said TSH, is increased.

According to a preferred embodiment, the invention relates to a kit as defined above, for assaying TSH in a biological sample, characterized in that it comprises:

at least one antibody selected from the group comprising S06 and B3, as capture antibody, at least one antibody selected from the same group comprising OCD1 and R2 as tracer antibody, and at least one glycoprotein calibrant which is selected from the group comprising a glycoform of recombinant TSH which is substantially more sialylated and/or more fucosylated than said recombinant TSH.

This kit is advantageous for assaying TSH from healthy subjects or from patients suffering from thyroid diseases, such as hypothyroidism, or from non-thyroid diseases coupled to altered levels of TSH; in this kit, the immunoassay involved is of format III/II, which is largely glycosylation dependent in that it may exhibit optimal binding capacity of TSH with altered and/or disease-related glycosylation.

A glycosylation-dependent assay is thereby defined by the use of antibodies which are able to capture the largest array of TSH glycoforms. Such assays can typically accommodate variation in sialic acid and/or fucose content and as a result, provide a better estimation of changes in hormone level compared to said glycosylation-independent assay.

The present invention also relates to a process for the preparation of a glycoform of a recombinant human TSH produced by mammalian cells, characterized in that said recombinant human TSH is sialylated by an α-2,6 sialyltransferase, in particular a human ST6GalI sialyltransferase, more particularly a N-terminal shortened human ST6GalI sialyltransferase deleted of at most its first 99 residues, such as represented by SEQ ID NO: 1, to yield an oversialylated glycoform of the recombinant TSH bearing α2,3 and α2,6 sialyl moieties.

In a preferred embodiment, the recombinant human TSH produced by mammalian cells, is produced by CHO cells.

In the human organism, TSH carries essentially only sulfated groups but has a low content in α2,3/6 linked sialic acid, the ratio of these sugars controlling hormone duration in blood. Thus it is advantageous to add α2,6 sialyl groups to the recombinant TSH, since most cell lines used for its production lack the adequate α2,6 sialyltransferase. For instance the recombinant TSH produced by the CHO cell line carries essentially only α2,3 sialyl groups.

In a particular embodiment of the above defined glycoform preparation process, the recombinant human TSH is first treated by a neuraminidase, in particular a *Clostridium perfringens* or a *Vibrio cholerae* neuramimidase, to give a substantially unsialylated TSH, and then submitted to sialylation, to yield a resialylated glycoform of the recombinant TSH bearing essentially only α2,6 sialyl moieties.

The present invention also relates to a process for the preparation of a glycoform of a recombinant human TSH produced by mammalian cells, characterized in that said recombinant human TSH is submitted to a lentil fractionation, to give a lentil unbound fraction and a lentil bound fraction, the lentil unbound fraction being retained to yield a substantially unfucosylated glycoform of the recombinant TSH and the lentil bound fraction being retained to yield a glycoform which is substantially more fucosylated than said recombinant TSH.

In a particular embodiment of the above mentioned glycoform preparation process:

the recombinant human TSH is submitted to neuramimidase treatment, in particular a *Clostridium perfringens* or a *Vibrio cholerae* neuraminidase, prior to lentil fractionation, or the lentil bound fraction or the lentil unbound fraction of the recombinant human TSH is submitted to neuraminidase treatment, to yield a substantially unsialylated substantially unfucosylated glycoform of the recombinant human TSH or a glycoform of the recombinant human TSH which is substantially unsialylated and substantially more fucosylated than said recombinant human TSH.

In a preferred embodiment of the above defined glycoform preparation process:

the recombinant human TSH is submitted to sialylation to give an oversialylated glycoform of the recombinant human TSH, or both to neuraminidase treatment and to sialylation to give a resialylated glycoform of the recombinant human TSH, prior to lentil fractionation of said glycoform, or the lentil unbound fraction or the lentil bound fraction of the recombinant human TSH is submitted to sialylation, or sequentially to both neuraminidase treatment and sialylation, to yield a substantially unfucosylated oversialylated or resialylated glycoform of the recombinant human TSH or a glycoform of the recombinant human TSH which is oversialylated or resialylated and substantially more fucosylated than said recombinant human TSH.

According to the invention, an oversialylated glycoform of a given glycoprotein comprises both the sialyl groups initially present on said glycoprotein and the new sialyl groups which have been added by the sialyltransferase treatment.

According to the invention, a resialylated glycoform of a given glycoprotein presents an homogenous sialylation state corresponding to the sialyltransferase which has been used; in particular, if an α2,6 sialyltransferase is used the resialylated glycoform comprises essentially only α2,6 sialyl groups.

The present invention also relates to a glycoform of recombinant human TSH such as obtainable according to the above mentioned glycoform preparation processes.

The present invention also relates to an oversialylated glycoform of a recombinant human TSH produced by mammalian cells which comprises from about 70% to about 100%

α2,3 and α2,6 sialyl groups, in particular from about 70% to about 85% α2,3 sialyl groups and from about 15% to about 30% α2,6 sialyl groups.

As intended herein, the sialylation percentage of a given glycoform relates to the number of sialyl groups it carries with respect to the maximum number of sialyl groups it is liable to carry. This sialylation percentage can be measured by sugar analysis and mass spectrometry as described in the following Examples. By way of example, in the case of a recombinant human TSH produced in CHO cells, the average maximum number of sialyl groups is 9.

It is possible to differentiate the percentage of α2,3 and α2,6 sialyl groups by using an α2,3-specific neuraminidase and/or and α2,6-specific neuraminidase.

The present invention also relates to a resialylated glycoform of a recombinant human TSH produced by mammalian cells which comprises from about 70% to about 100% α2,6 sialyl groups.

The present invention also relates to a glycoform of a recombinant human TSH produced by mammalian cells which comprises essentially no fucose.

The present invention also relates a glycoform of a recombinant human TSH produced by mammalian cells which comprises from about 30% to about 100% fucose.

As intended herein, the fucosylation percentage of a given glycoform relates to the number of fucose groups it carries with respect to the maximum number of fucose groups it is liable to carry, that is 3. This fucose percentage can be measured by sugar analysis and mass spectrometry as described in the following Examples.

In a preferred embodiment, the glycoform of recombinant human TSH produced by mammalian cells comprises essentially no fucose and no sialyl groups.

In another preferred embodiment, the glycoform of recombinant human TSH produced by mammalian cells comprises essentially no sialyl groups and from about 30% to about 100% fucose.

In another preferred embodiment, the glycoform of recombinant human TSH produced by mammalian cells comprises from about 70% to about 100% α2,3 sialyl and α2,6 sialyl groups, in particular from about 70% to about 85% α2,3 sialyl groups and from about 15% to about 30% α2,6 sialyl groups, and essentially no fucose.

In another preferred embodiment, the glycoform of recombinant human TSH produced by mammalian cells comprises from about 70% to about 100% α2,6 sialyl groups and essentially no fucose.

In another preferred embodiment, the glycoform of recombinant human TSH produced by mammalian cells comprises from about 70% to about 100% α2,3 sialyl and α2,6 sialyl groups, in particular from about 70% to about 85% α2,3 sialyl groups and from about 15% to about 30% α2,6 sialyl groups and from about 30% to about 100% fucose.

In another preferred embodiment, the glycoform of recombinant human TSH produced by mammalian cells comprises from about 70% to about 100% α2,6 sialyl groups and from about 30% to about 100% fucose.

In a preferred embodiment of the above mentioned glycoforms, the recombinant human TSH produced by mammalian cells, is produced by CHO cells.

These above mentioned glycoforms of recombinant TSH are advantageous in that their recognition pattern by anti-TSH antibodies is highly similar to the recognition pattern of the natural plasma TSH found in the human organism.

The present invention also relates to a kit for assaying specific glycoforms of a first glycoprotein, characterized in that it comprises at least one antibody such as screened according to the above mentioned glycoform-specific antibody screening process.

According to a preferred embodiment of the above defined kit, the kit is intended for assaying TSH in a biological sample and is characterized in that it comprises:
at least one capture-antibody selected from pools Ia, Ib, or III,
at least a tracer-antibody selected from pools Ib, II, or III, provided that the capture-antibody and the tracer-antibody do not belong to the same pool, wherein:
pool Ia is defined as being the pool of antibodies which can not bind to TSH once antibody, B1, S04 or BC27 has already been bound to it,
pool Ib is defined as being the pool of antibodies which can not bind to TSH once antibody B2, R1 or S09 has already been bound to it,
pool II is defined as being the pool of antibodies which can not bind to TSH once antibody OCD1 or R2 has already been bound to it,
pool III is defined as being the pool of antibodies which can not bind to TSH once antibody B3 or S06 has already been bound to it.

In another preferred embodiment, the above defined kit comprises:
a capture-antibody selected from pool Ia and a tracer antibody selected from pool Ib, or
a capture-antibody selected from pool Ia and a tracer antibody selected from pool II, or
a capture-antibody selected from pool Ib and a tracer antibody selected from pool II, or
a capture-antibody selected from pool Ia and a tracer antibody selected from pool III, or
a capture-antibody selected from pool Ib and a tracer antibody selected from pool III, or
a capture-antibody selected from pool III and a tracer antibody selected from pool II.

In a particularly preferred embodiment, the above defined kit further comprises a calibrant selected from the list comprising:
pituitary human TSH, recombinant human TSH produced by mammalian cells, a glycoform of recombinant human TSH produced by mammalian cells which substantially less sialylated than said recombinant human TSH, a glycoform of recombinant human TSH produced by mammalian cells which is substantially more sialylated and/or less fucosylated than said recombinant human TSH, and a glycoform of recombinant human TSH as defined above.

As intended herein a "calibrant" relates to a glycoprotein which presents an antibody binding pattern essentially similar to that of the glycoprotein intended to be assayed by the kit. Thus, the calibrant is used to standardize the immunological assays.

The present invention also relates to the use of a glycoprotein selected from the list comprising:
a glycoform of recombinant human TSH produced by mammalian cells which is substantially less sialylated than said recombinant human TSH, a glycoform of recombinant human TSH produced by mammalian cells which is substantially more sialylated and/or less fucosylated than said recombinant human TSH, and a glycoform of recombinant human TSH as defined above.
for calibrating TSH immunoassays.

The present invention also relates to a shortened human ST6GalI sialyltransferase lacking the first 89 N-terminal residues with respect to the wild type human ST6GalI, as represented by SEQ ID NO: 1.

Such a shortened ST6GalI sialyltransferase is advantageous over that of the prior art, because of its increased solubility and of its superior activity.

DESCRIPTION OF THE FIGURES

FIGS. 1A to 1D represent the typical glycosylation patterns of the major glycoforms found for N-linked glycoproteins (FIG. 1A), human pituitary TSH (pitTSH) (FIG. 1B), the recombinant TSH (recTSH) used herein (FIG. 1C), and the putative human plasma TSH thought to be the disease-related form of TSH circulating in hypothyroid patient (FIG. 1D). Asn-X-Ser/Thr corresponds to the consensus peptide sequence for N-glycosylation. NeuAc corresponds to sialic acid linked to the glycan chain by α2,3 or α2,6 linkages. The grey diamond shapes correspond to fucose, the white squares to N-acetylglucosamine, the grey circles to mannose, the black circles to galactose and the grey triangle to N-acetylgalactosamine.

FIG. 2A-D represent the epitope screening of recTSH as obtained by a sandwich ELISA test, using antibodies BC27, B1, B2, B3, R1, R2, S04, S06, and S09 as capture antibodies and biotinylated-OCD1 as a tracer antibody (FIG. 2A), biotinylated-BC27 as a tracer antibody (FIG. 2B), biotinylated-S04 as a tracer antibody (FIG. 2C), biotinylated-S06 as a tracer antibody (FIG. 2D). In FIG. 2A a negative control is also provided (T(−)).

FIG. 3 is a simplified diagrammatic representation of the various epitopic regions (I, II and E) recognized by the BC27, B1, B2, B3, R1, R2, S04, S06, S09 and OCD1 antibodies, as deduced from the epitope screening of recTSH. S06 and B3 recognize overlapping epitopes located in epitopic region III; OCD1 and R2 recognize different epitopes located in epitopic region II; S09, R1 and B2 recognize virtually similar epitopes located in epitopic region I, which are different from the epitope recognized by BC27 and the essentially similar epitopes recognized by S04 and B1, in the same epitopic region I.

FIGS. 4A to 4F represent sandwich ELISA assays of IRP pitTSH (black diamond shapes), IRP recTSH (black squares) and oversialylated recTSH (white squares). The horizontal axis represents the concentration of TSH (in IU/L) and the vertical axis the OD at 405 nm. FIG. 4A corresponds to a I/II format (capture antibody BC27, tracer antibody OCD1), FIG. 4B corresponds to a II/I format (capture antibody R2, tracer antibody S04), FIG. 4C corresponds to a I/III format (capture antibody BC27, tracer antibody S06), FIG. 4D corresponds to a III/I format (capture antibody S06, tracer antibody S04), FIG. 4E corresponds to a II/III format (capture antibody R2, tracer antibody S06) and FIG. 4F corresponds to a III/II format (capture antibody S06, tracer antibody OCD1). As intended herein 1 μg of TSH corresponds to 4.93 mIU.

FIGS. 5A-C represent ELISA assays of various TSH preparations varying in sialic acid content. The horizontal axis represents the concentration of TSH (in IU/L) and the vertical axis the OD at 405 nm. The black squares correspond to IRP recTSH, the black triangles to asialo-recTSH, the black diamond shapes to IRP pitTSH, the white squares to oversialylated recTSH (recTSH sialylated with α2,6 sialyltransferase) and the white triangles to resialylated recTSH (asialo-recTSH treated with α2,6 sialyltransferase). FIG. 5A represents the results of the S06-BC27 sandwich, FIG. 5B the results of the BC27-OCD1 sandwich and FIG. 5C a control measurement of α2,6-linked sialic acid using *Sambucus nigra* (SNA) lectin binding. As intended herein 1 μg of TSH corresponds to 4.93 mIU.

FIG. 6A represents the kinetics of OCD1 binding to TSH preparations in a BC27-OCD1 sandwich ELISA assay. The horizontal axis represents the incubation time with OCD1 in minutes and the vertical axis the OD at 405 nm. The black squares correspond to IRP recTSH, the black triangles to asialo-recTSH, the black diamond shapes to IRP pitTSH, the white squares to oversialylated recTSH (recTSH treated with α2,6 sialyltransferase) and the white triangles to resialylated recTSH (asialo-recTSH treated with α2,6 sialyltransferase).

FIG. 6B represents a SNA binding assay of the previous TSH preparation (horizontal axis) as measured by the OD at 405 nm (vertical axis).

FIGS. 7A and 7B represent lectin affinity chromatography profiles for recTSH detected with III/I format (S06-BC27). In FIG. 7A an unbound fraction (eluted by TBS) and a bound fraction (eluted by 500 mM α-methylmannopyranoside) are shown. The bound fraction is enriched in fucosylated recTSH as compared to the unbound fraction.

In FIG. 7B, three fractions are shown, an unbound fraction (eluted by TBS), a weakly bound fraction (eluted by 10 mM α-methylglucopyranoside) and a firmly bound fraction (eluted by 500 mM α-methylmannopyranoside). The three fractions differ from each other with respect to their respective branching states.

FIGS. 8A and 8B represent sandwich ELISA assays of recTSHs purified by lentil affinity chromatography using the BC27-OCD1 format (FIG. 8A) and the S06-S04 format (FIG. 8B). The horizontal axes represent the concentration of TSH (in IU/L) and the vertical axes the OD at 405 nm. The black squares represent IRP recTSH, the black cross IRP pitTSH, the black diamond shapes the lentil unbound fraction of recTSH and the black triangles the lentil bound fraction of recTSH. As intended herein 1 μg of TSH corresponds to 4.93 mIU.

FIGS. 9A and 9B represent the kinetics of antibody binding to lentil-chromatography fractions for S06 binding in S06-S04biot assay (FIG. 9A) and for S04 binding in S06-S04biot assay (FIG. 9B). The horizontal axes represent the time in minutes and the vertical axes represent the OD at 405 nm. The black crosses represent IRP pitTSH, the black squares recTSH, the black diamond shapes the lentil unbound fraction and the black triangles the lentil bound fraction.

FIGS. 10A-D represent the effect of the TSH branching pattern on antibody binding using the BC27-OCD1 (FIG. 10A), S06-OCD1 (FIG. 10B), S06-S04 (FIG. 10C) and BC27-S06 (FIG. 10D) formats. The horizontal axis represents the concentration of TSH (in IU/L) and the vertical axis the OD at 405 mm. The black diamond shapes correspond to the ConA unbound fraction, the black squares to the weakly bound fraction, the black triangles to the firmly bound fraction, and the black crosses to IRP pitTSH. As intended herein 1 μg of TSH corresponds to 4.93 mIU.

FIG. 11A represents the percentage of oversialylated recTSH (vertical axis) in the unbound fraction (black bars), the weakly bound fractions (white bars) or the firmly bound fractions (hatched bars) of a ConA fractionation of oversialylated recTSH according to the indicated sandwich ELISA formats.

FIG. 11B represents the percentage of oversialylated recTSH (vertical axis) in the unbound fraction (black bars), or the bound fractions (hatched bars) of a lentil fractionation of oversialylated recTSH according to the indicated sandwich ELISA formats.

FIGS. 12A-C represent the plateau charge (vertical axis, OD at 405 nm) of the indicated sandwich ELISA formats (horizontal axis) for IRP pitTSH (FIG. 12A), IRP recTSH (FIG. 12B) and oversialylated recTSH (FIG. 12C).

FIGS. 13A and 13B represent the ELISA assays of TSH varying in core-fucose content. The horizontal axes represent the volume of lentil fraction tested (in µL) and the vertical axes the OD at 405 nm. Diamonds correspond to the BC27-OCD1 format, squares to S06-S04, and triangles to S06-OCD1. Figure A represents the results obtained with the unbound fraction of lentil chromatography (non fucosylated oversialylated recTSH), and figure B the results obtained with the bound fraction of lentil chromatography (fucosylated oversialylated recTSH).

FIGS. 14A to 14D represent the comparative analysis of TSHs from pituitary and recombinant origin based on MALDI-TOF mass spectrometry. Subunits of a highly purified preparation of pituitary TSH (FIG. 14A) were identified using free subunits. Recombinant TSH is represented in FIG. 14B, asialo-recTSH in FIG. 14C and recTSH enzymatically sialylated with the engineered human α2,6-sialyltransferase ST6GalI produced in CHO cells in FIG. 14D.

FIGS. 15A-15D represent the epitope screening of pituitary TSH (pitTSH) and recombinant TSH (recTSH) as obtained by a sandwich ELISA test, using antibodies BC27, B1, B2, B3, R1, R2, S04, S06, and S09 as capture antibodies and biotinylated-OCD1 as a tracer antibody (FIG. 15A), biotinylated-BC27 as a tracer antibody (FIG. 15B), biotinylated-S04 as a tracer antibody (FIG. 15C), biotinylated-S06 as a tracer antibody (FIG. 15D).

FIG. 15E represents a schematic map of the various epitopic regions of TSH designed as I, II and III respectively. Binding experiments were conducted at equilibrium in presence of saturating conditions of TSH (10 ng). S06 and B3 recognize overlapping epitopes located in epitopic region III; OCD1 and R2 recognize different epitopes located in epitopic region II. S04 and B1 recognized similar epitopes in the epitopic region I, overlapping the area bound by BC27 (region Ia). Together with S09, R1 and B2 which target virtually similar epitopes which are different from the epitope recognized by BC27 as well as B1 and S04, but still in region I (region Ib).

FIGS. 16A, 16B and 16C represent the maximal binding capacity of various TSH preparations in the I-I, I-III and II-III formats. Maximal values were deduced from FIGS. 4A to 4F (vertical axis) for the $2^{nd}$ IRP pitTSH (FIG. 16A), the $1^{st}$ IRP recTSH (FIG. 16B) and oversialylated recTSH (FIG. 16C) respectively, and their respective EC50 values for $2^{nd}$ IRP pitTSH in FIG. 16D, $1^{st}$ IRP recTSH in FIG. 16E and oversialylated recTSH in FIG. 16F.

FIG. 17 represents the distribution of oversialylated recTSH on Lentil-Sepharose has been expressed as percentage of the total recovery in assays as indicated. All assays have been calibrated with recTSH on a molar basis. UB refers to unbound (non fucosylated) fractions and B to bound (fucosylated) fractions. Binding experiments were conducted overnight at equilibrium at 4° C.

FIG. 18 represents the distribution of oversialylated recTSH on Con A-Sepharose expressed as a percentage of total recovery. The indicated assays have been calibrated with the recTSH on a molar basis and incubated overnight at equilibrium at 4° C. UB refers to the unbound fraction (TSH with multiantennary glycans), WB to the weakly bound fraction of TSH containing at least one biantennary glycan and FB to the firmly bound TSH fraction which reflects the cooperative binding of several glycans by the tetravalent lectin.

FIGS. 19A, 19C and 19E were obtained with biotinylated BC27 antibody as tracer, and FIGS. 19B, 19D and 19F with biotinylated S04 antibody as tracer. Binding experiments were carried out at the EC50 (2 ng TSH) at equilibrium. Capture antibodies are presented on the horizontal axes and OD at 405 nm on the vertical axes. Pituitary TSH is represented in white, recombinant in black and blood TSH in grey.

FIGS. 19G to 19L represent the quantitative epitope oriented mapping of pituitary, recombinant and blood TSH using tracer antibodies directed against epitope II. FIGS. 19G, 19I and 19K were obtained with OCD1 antibody as tracer, and FIGS. 19H, 19J and 19L with biotinylated R2 antibody as tracer. Binding experiments were carried out at the EC50 (2 ng TSH) at equilibrium. Capture antibodies are presented on the horizontal axes and OD at 405 nm on the vertical axes. Pituitary TSH is represented in white, recombinant in black and blood TSH in grey.

FIGS. 19M-19O represent the quantitative epitope oriented mapping of pituitary, recombinant and blood TSH using tracer antibodies directed against epitope III. FIGS. 19M, 19N and 19O were obtained with S06 antibody as tracer. Binding experiments were carried out at the EC50 (2 ng TSH) at equilibrium. Capture antibodies are presented on the horizontal axes and OD at 405 nm on the vertical axes. Pituitary TSH is represented in white, recombinant in black and blood TSH in grey.

FIGS. 20A-20C summarize the immunological behavior of the various TSHs in the 32 formats described by the invention. FIG. 20A describes the respective potency of recTSH compared to pitTSH. FIG. 20B describes the respective potency of bloodTSH compared to pitTSH. FIG. 20C describes the respective potency of bloodTSH compared to recTSH.

EXAMPLES

Example 1

Immunological Characterization of a Recombinant Glycoprotein: TSH

A panel of monoclonal antibodies elicited against human pituitary TSH (pitTSH) were screened against glycoforms of a preparation of recombinant TSH (recTSH), each glycoform corresponding to a determined glycosylation state defined by a modification of the glycosylation pattern typically in either sialylation, fucosylation or branching.

The following monoclonal antibodies elicited against human pituitary TSH were used: OCD1 (Ortho-Clinical Diagnostics, USA), BC27 (Beckman-Coulter, USA), R1 and R2 (Roche Diagnostics), S04, S06 and S09 (Seradyn, USA), B1, B2 and B3 (Bayer Diagnostics).

Prior to use, the antibodies were biotinylated according to the manufacturer recommendations as follows: 200 µg mAb to be biotinylated, were incubated with 6 µg biotin-7-NHS/DMSO, 2 h at room temperature during gentle stirring. Remaining non reacted biotin-7-NHS was separated by gel filtration on a Sephadex G-25 column previously blocked and washed. Labeled antibody was then eluted with PBS solution, the extinction at 280 nm of collected fractions was measured and conjugates concentration determined according to $OD_{280} = \epsilon \times C \times 1$ with extinction coefficient $\epsilon = 1.35$ for mAbs. Eluates containing the conjugate were then pooled.

The recombinant TSH (recTSH) was from Seradyn (USA), and the pituitary TSH (pitTSH) was from Biogenesis (UK).

The following materials and reagents were also used. IRP (International Reference Preparations) standards ($2^{nd}$ IRP pitTSH (80/558) and $1^{st}$ IRP recTSH (94/674)) were ordered at the NISBC (National Institute for Biological Standards and Control, UK). Neuraminidase, asialofetuin, bovine serum albumin (BSA), α-methyl glucopyranoside, α-methylmannopyranoside, cacodylic acid, Triton X-100, CMP-NeuAc, p-NitroPhenylphosphate (p-NPP) and Tween 20 were purchased from SIGMA. SNA-biotin was from Vector Laboratories and the streptavidin-alkaline phosphatase conjugate from Jackson ImmunoResearch Laboratories. Purified rat liver ST6Gal I and biotin labeling kit were from Roche. ConA-Sepharose and Lentil-Sepharose were from Pharmacia Biotech, and chromatography columns from VWR International as well as microtiter 96-wells plates. All culture reagents were from INVITROGEN-Life Technologies. The Micro BCA™ Protein Assay Kit was from Pierce (Perbio).

Figure 1A:
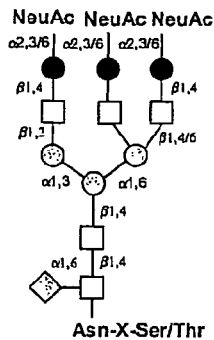
FIG. 1A, FIG. 1B, FIG. 1C and FIG. 1D
Figure 1B:
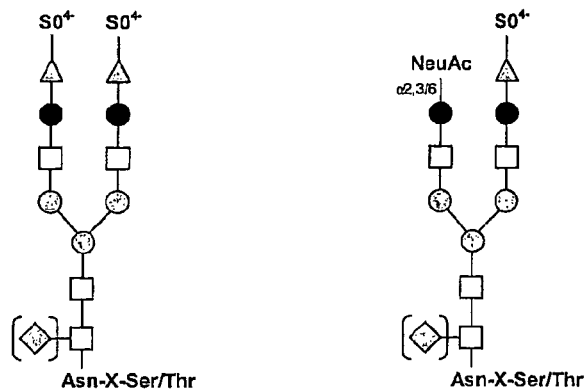
Figure 1C:
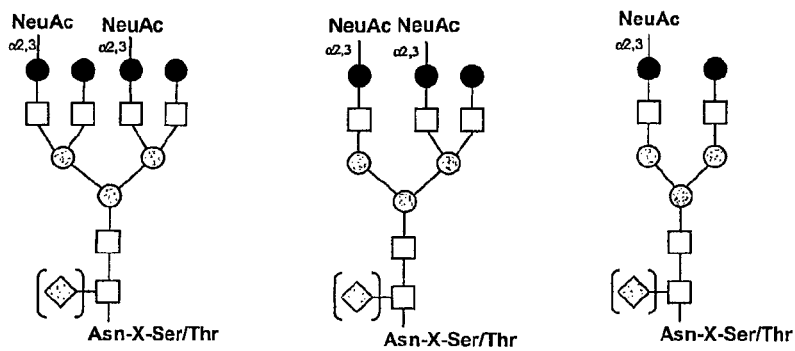
Figure 1D:
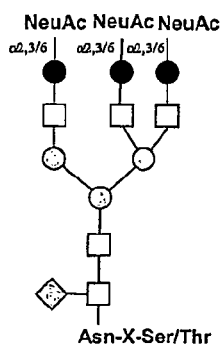

The commercial preparation of recTSH was investigated to identify the whole array of glycan structure present in the product. Since many structural features were reported to differ between pitTSH and various preparations of recTSH (Grossmann, M. et al., 1995; Canonne, C. et al., 1995) as well as between the pituitary stock and the circulating hormone in normal subjects or patients with thyroid disorders (Papandreou, M-J., et al., 1993), it was of definite interest to understand how far glycosylation of recTSH may be altered compared to the native hormone. FIGS. 1B-1D thus represents the first elucidation of the kind applied to TSH.

The glycosylation pattern of the recTSH used was first investigated (Morelle, W., and Michalski, J. C., unpublished results). As expected for a compound expressed in mammalian cells which do not contain the enzymatic machinery for synthesizing the GalNAc-sulfate signal, no such sulfated signal was found in the product. Neither hybrid nor mannose-rich was observed like in the pituitary stock either. Such glycans are often present in pitTSH because the pituitary extract contains immature forms of the hormone. Rather, only serum-type glycans were identified in recTSH, ranging from biantennary to tetraantennary structure, containing inner fucose and terminated in sialic acid.

This glycan pattern is in full agreement with the pattern recently observed for gonadotropins produced in CHO cells (Gervais, A., et al., 2003), indicating that the engineered hormone is appropriately glycosylated with complex glycans by the host system but that some control is nevertheless lacking as the final product is quite different in glycosylation from the native hormone. The putative structure of plasma TSH is also represented in FIG. 1D.

It is well established that mammalian cells of non-pituitary origin can provide a serum-type glycosylation and thus had the potentiality to contain the various changes in glycan structure known to occur in the hormone upon secretion in blood and metabolic clearance as summarized in FIGS. 1A-1D. Since it has been previously reported that circulating TSH was highly sialylated and enriched in multiantennary glycans (Papandreou, M. J., et al., 1993), the Inventors therefore hypothesized that this compound might be a good candidate to further engineer mimics of plasma and disease-related TSH.

Briefly, MALDI-TOF mass spectra were recorded on a Voyager DE-RP (Applied Biosystems, CA, USA), in a positive ion linear mode with a delayed extraction. A saturated solution of matrix was prepared by diluting 10 mg of 3,5-dimethoxy-4-hydroxycinnamic (sinapinic acid) in 500l of 0.1% trifluoroacetic acid in water and acetonitrile (40/60, V/V). 0.7-1 µl of the sample solution was applied to a stainless steel sample plate for MALDI-MS, then 0.7 µl of the matrix solution was added and the mixture was allowed to dry at room temperature. Mass calibration was done on a standard horse apomyoglobin solution using its monocharged ion [M+H]+ at 16951.56 and its double charged ion [M+2H]2+/2 at 8476.28. Mass spectra were then treated by a Gaussian smoothing with a filter width at 19 points.

It is reminded that the intensity of the signals (height of the peaks) is poorly related to the quantity of each species and that essentially qualitative values on molecular size of the entities can be interpretated.

Figure 14A:
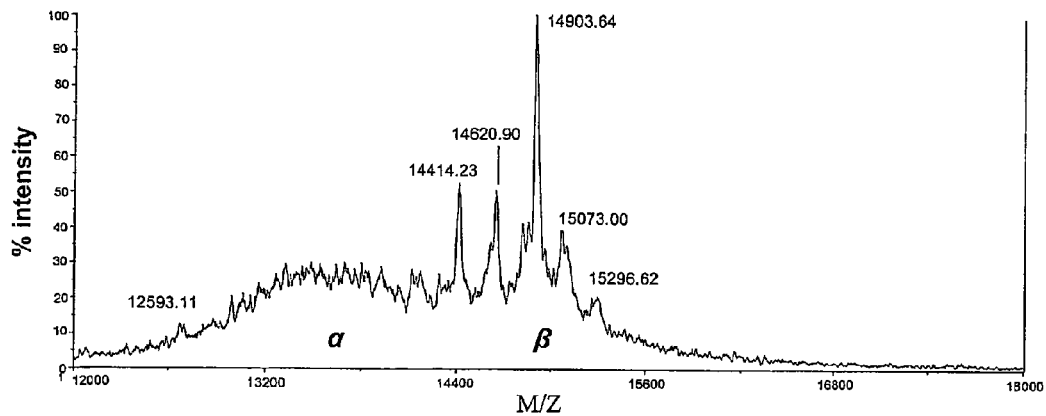
FIG. 14A, FIG. 14B, FIG. 14C, FIG. 14D
Figure 14B:
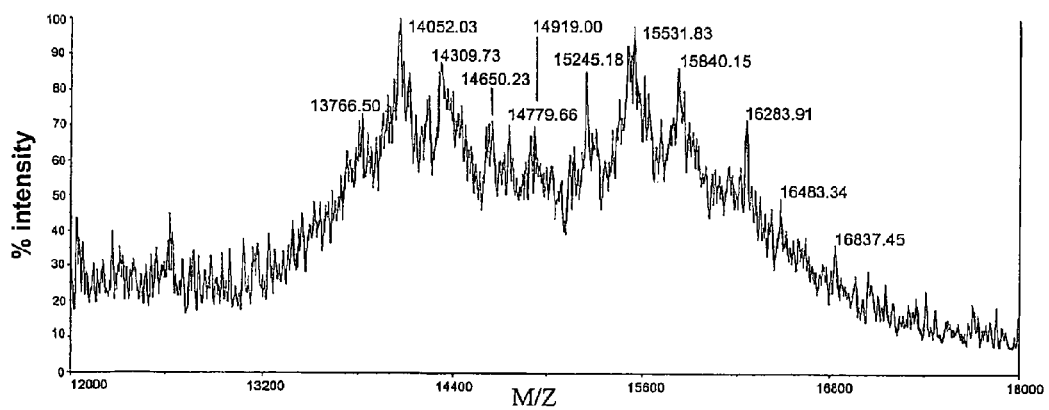
Figure 14C:
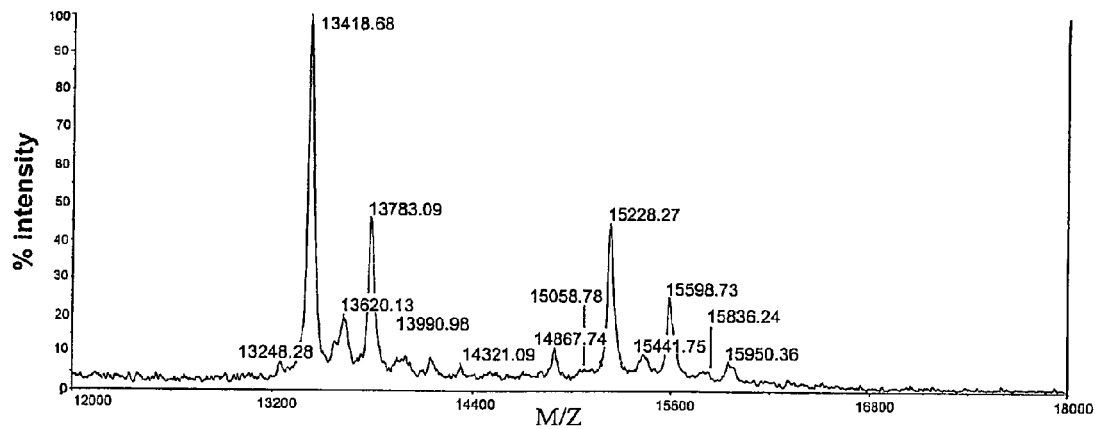
Figure 14D:
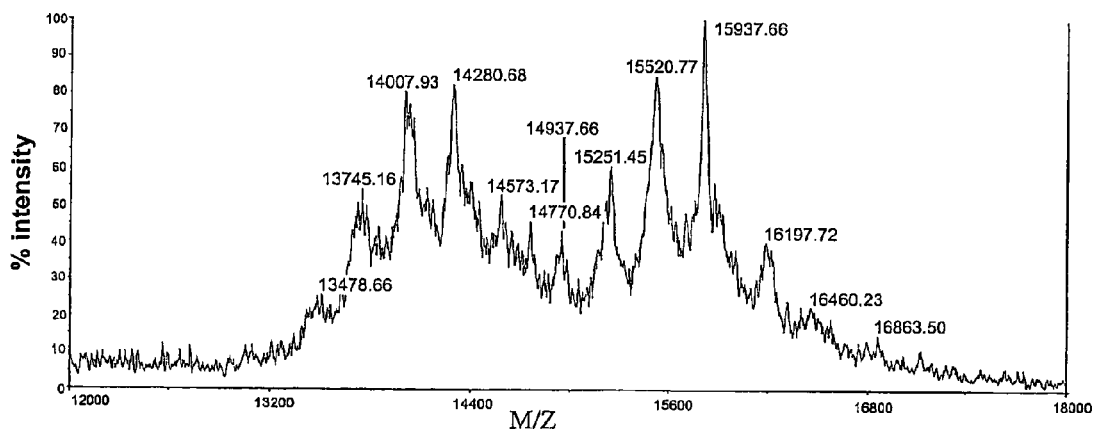

As shown in FIG. 14A, both TSH subunits have been estimated separately using free pitTSH subunits. The α subunit appeared highly heterogeneous (12.6-14.6 kDa) because it contains 2 N-glycans while the β-subunit was resolved as 5 main species ranging from 14.6 kDa to 15.3 kDa in size. In contrast, all subunit species appeared of increased molecular weight in the recombinant product (FIG. 14B), suggesting profound changes in glycosylation in both subunits since these two compounds share the same peptide sequence. In addition, recTSH microheterogeneity was definitely augmented as a result of increased sialic acid content because treatment with neuraminidase shifted and simplified the profile of both subunits to half a dozen of entities for the asialo α-subunit (13.4-13.9 kDa) and asialo β-subunit (14.8-15.9 kDa) as shown in FIG. 14C. Enzymatic resialylation of recTSH (see hereafter) with an engineered α2,6 sialyltransferase reproduced the original pattern (FIG. 14D), indicating that sialic acid (approx. 300 Da per residue) has been transferred virtually onto both asialo subunits (FIGS. 14C and 14D).

Since the glycans of recTSH cover a wide array of structure totally different from those of the pituitary stock, the glycoforms onto which they are present can be regarded as putative markers of altered glycosylation. Accordingly, the whole recTSH preparation could be used to assess to what extent changes in glycan structure affect antibody recognition. The Inventors therefore screened a panel of 10 different monoclonal antibodies specific for human TSH ($\leq 0.2\%$ cross-reactivity with gonadotropins) against a highly purified preparation of pitTSH and recTSH. Antibodies specific for TSH were commonly elicited from a pituitary preparation and selected to recognize this hormone in blood samples with high specificity i.e. with virtually no cross-reactivity with gonadotropins or free alpha subunits. Earlier on, two preparations of recTSH were reported to compete with pitTSH for antibodies directed against pituitary TSH (Kashiwai, T., et al., 1991) indicating that distinct preparations of TSH may indeed share cross-reactivity.

As shown in Table I, the antibodies could be classified into three groups, depending on their binding to recTSH to a similar (group A), different (group B) or lower extent (group C) than pitTSH at half-maximal binding capacity. Most antibodies differentially recognized the two preparations, indicating that they target determinants which are under direct or indirect control of glycosylation in the hormone antigen. Since the glycans found in recTSH are typically representative of serum-type glycoproteins in mammals; none of them are antigenic. It results that mAbs are directed against peptidic regions under the steric control of glycan chains. Similar recognition of both preparations was observed in group A (mAb BC27) indicates that at least the underlying epitope is similarly expressed in both preparations. Interestingly, some antibodies like mAbs S06 and R2 displayed increased recognition of recTSH, suggesting that changes in glycosylation may generate epitope expression in glycoforms which are masked or absent in the pituitary preparation. In contrast, the recombinant product is poorly recognized by group C antibodies (mAbs B3 and OCD1), because their epitopes are poorly displayed in the antigen.

TABLE I

Differential screening of anti-TSH antibodies:

| | mAbs | pitTSH | recTSH |
|---|---|---|---|
| Group A "High binding" | BC27 | ++++ | ++++ |
| Group B "Medium binding" | R1 | ++++ | +++ |
| | S09 | ++ | +++ |
| | S06 | + | +++ |
| | R2 | + | +++ |
| | B1 | +++ | ++ |
| | S04 | ++ | ++ |
| | B2 | + | ++ |
| Group C "Low binding" | B3 | + | + |
| | OCD1 | +++ | + |

Since no information is available for any other antigen in the literature as to whether these findings may be of relevance for improving measurement accuracy, the Inventors were prompted to elucidate the number and location of the common epitopes shared by pitTSH and recTSH which may be useful to design innovative specific assays as the measurand will be clearly identified.

Figure 2A:
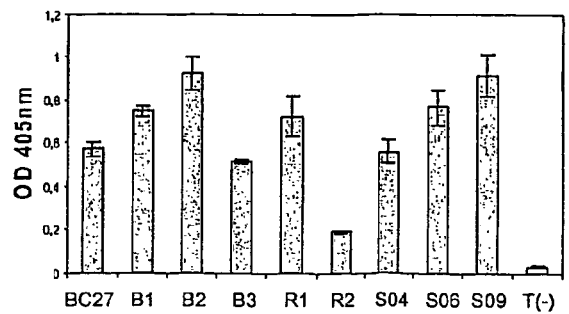
FIG. 2A, FIG. 2B, FIG. 2C and FIG. 2D
Figure 2B:
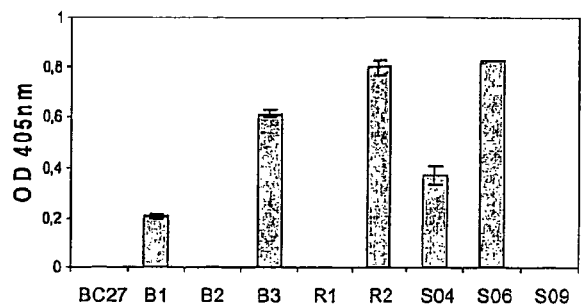
Figure 2C:
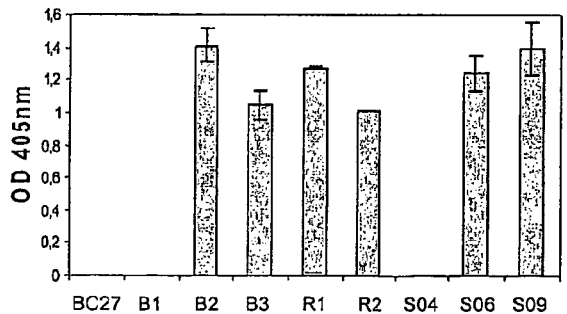

The same panel anti-TSH antibodies were further used to construct different sandwich formats to establish the epitope map of the recombinant hormone. The capture antibody was unmodified while the tracer antibody was biotinylated and the sandwich amplified using the streptavidin-alkaline phosphatase conjugate. All the experiments were carried out at equilibrium in the presence of excess of hormonal ligands. The results were read by measuring the OD at 405 nm. FIG. 2A-C summarizes the data.

ELISA experiments were carried out as previously described (Canonne, C., et al., 1995). Briefly microtiter plates were coated with monoclonal anti-TSH antibody (1 µg) in 100 µL PBS (50 mM, pH 7.5) for 2 hr at 37° C. Washings were performed after each step with PBS containing 0.05% Tween 20. Saturation was performed with 2% BSA-PBS. Increasing concentration of either TSH preparations or lectin fractions were incubated in PBS containing 0.1% BSA overnight at 4° C. or for shorter periods of time at 37° C. as indicated. Bound TSH was detected with the tracer anti-TSH mAb coupled to biotin (100 ng). Amplification was based on the streptavidin-alkalin phosphatase conjugate and p-NPP substrate as in Legaigneur et al. (2001). All the assays were performed in duplicates and the data expressed as a mean of these values.

Figure 2D:
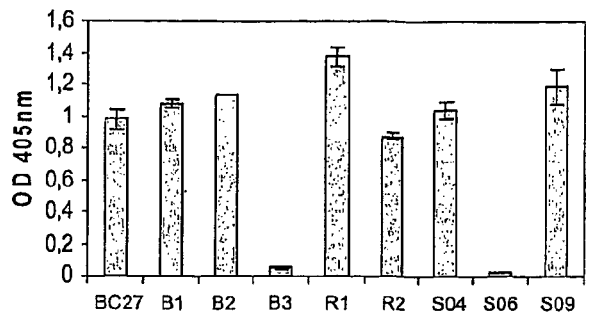
Figure 3:
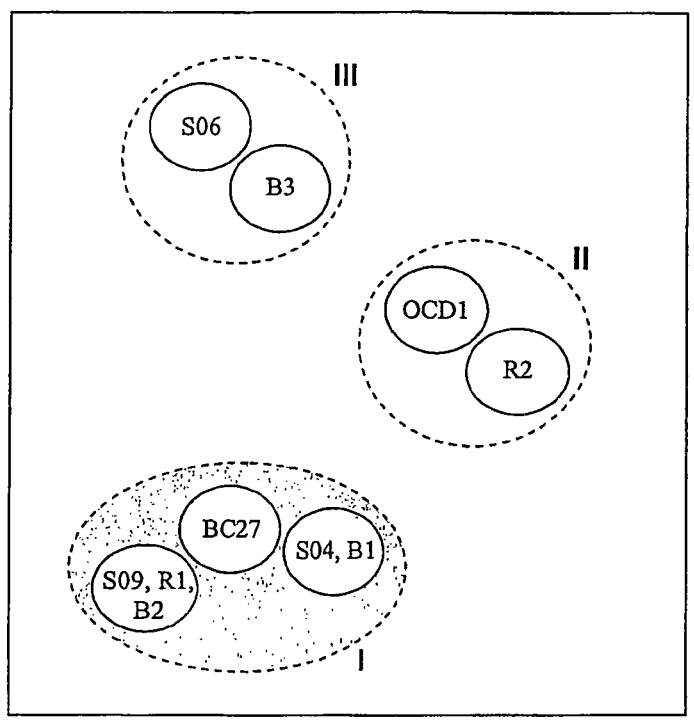
FIG. 3
Figure 4A:
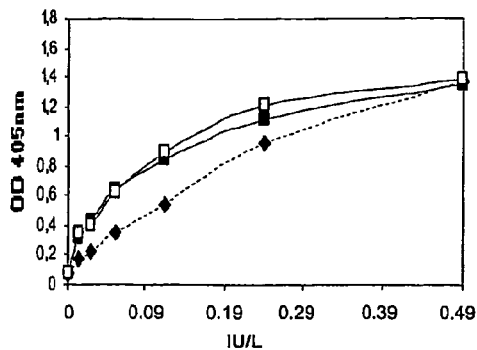
FIG. 4A, FIG. 4B, FIG. 4C, FIG. 4D, FIG. 4E and FIG. 4F
Figure 4B:
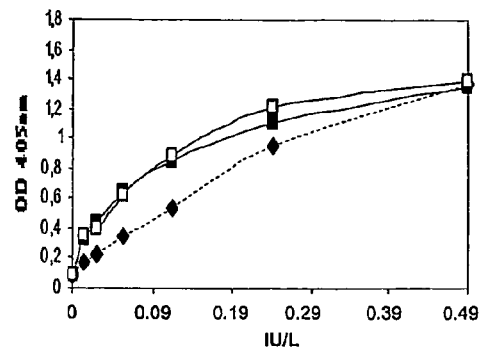
Figure 4C:
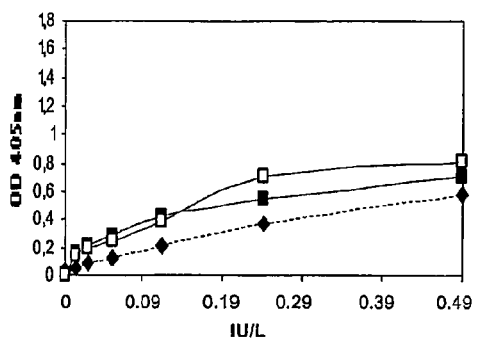
Figure 4D:
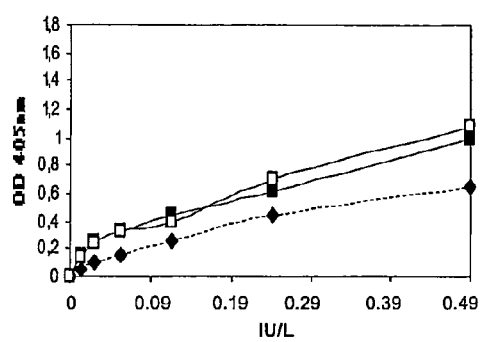
Figure 4E:
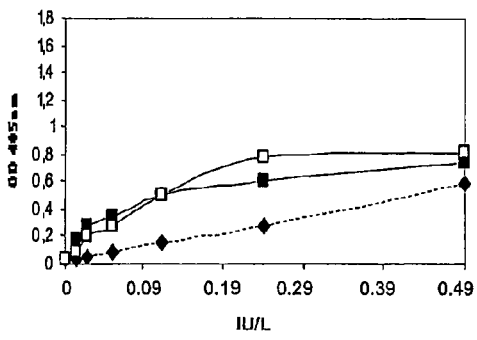
Figure 4F:
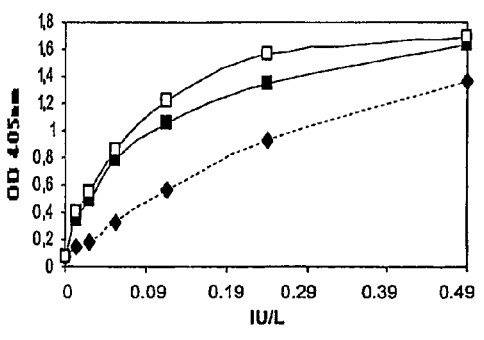

In FIG. 2A, OCD1 was found to bind recTSH independently of the others and partially overlap with R2. In contrast (FIG. 2B), mAb BC27 appeared to bind the same epitope as mAbs B2, R1 and S09. The determinant bound by mAbs S04 and B1 should either similar or in close vicinity (FIG. 2C) while the binding of B3 overlapped with that of S06 (FIG. 2D). These data allowed the Inventors to delineate within recTSH, 3 distinct epitopes designed as I, II and III respectively common to both pitTSH and recTSH. The main characteristic feature of these epitopes is that they can be identified by antibodies directed against the natural hormone with high specificity. As shown in FIG. 3, epitope I is very likely to be the Main Immunogenic Region (MIR) as it is recognized by most antibodies of the panel. Since R2, OCD1 and S06 bound the two TSHs to a different extent, epitopes II and III are likely to exhibit variable expression in the two preparations tested.

Figure 15A:
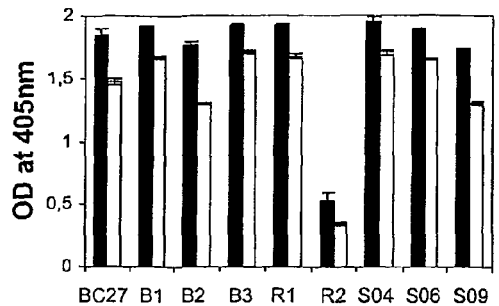
FIG. 15A, FIG. 15B, FIG. 15C, FIG. 15D and FIG. 15E
Figure 15B:
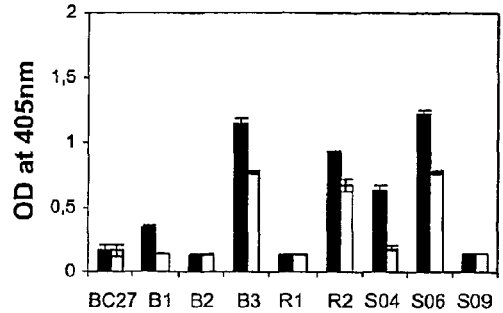
Figure 15C:
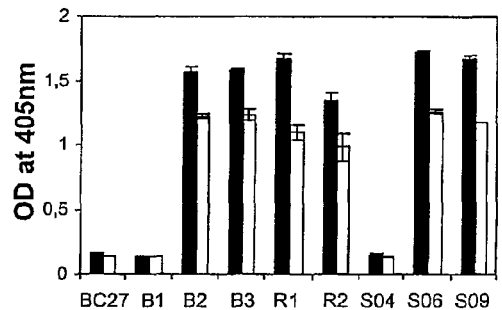
Figure 15D:
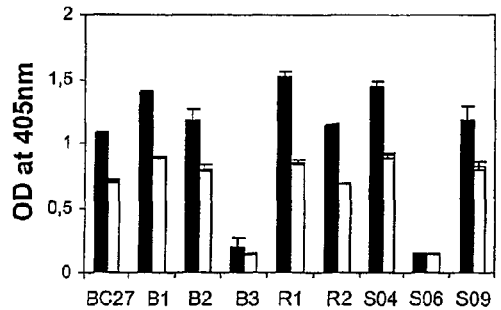

The panel of 10 specific monoclonal antibodies was then used to perform a comparative epitope map of pit- and recTSH based on the use of the 36 sandwich formats. The data are presented in FIGS. 15A-15D and summarized in FIG. 15E. In FIG. 15A, the mAb (OCD1) tracer was found to bind very similarly both antigens independently of the others and partially overlap with mAb (R2). In contrast (FIG. 15B), mAb (BC27) bound rather weakly both TSHs and shared the same epitope with mAbs (B1), (B2), (R1) and (S09). FIG. 15C shows that the determinant bound by mAb (S04) should be in close vicinity of that of mAbs (BC27) and (B1). In FIG. 15D, it can be seen that the binding of mAb (133) overlapped that of mAb (S06). Of note, the binding capacity of pitTSH could be reduced as much as 50% compared to recTSH, as in assays using mAbs (R1) and (S04) with (S06) mAb as tracer (FIG. 15D). This indicated that antibodies may display preference for TSH subforms in these preparations.

Figure 15E:
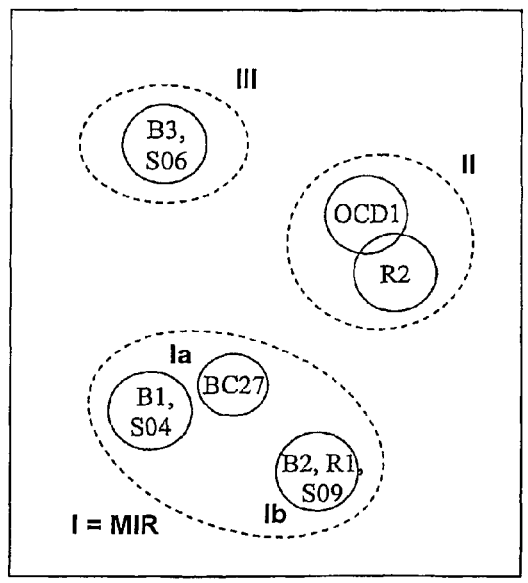

As summarized in FIG. 15E, anti-TSH mAbs target 3 main antigenic regions common to both pit- and recTSH, further designed as I, II and III respectively.

Based on these observations, the Inventors therefore decided to construct two novel types of TSH measurements: a first one tentatively aimed at equally measuring forms present in both pit- and recTSHs i.e. independently of changes in their glycosylation pattern. Another one designed as glycosylation-dependent, more likely to measure alteration in the antigen potentially related to a putative onset of a thyroid disorder. To this aim, they therefore designed and tested the all 6 possible assay formats with the 3 epitopes (I, II and III) namely I/II, II/I, I/III, III/I, II/III, III/II, based on the calibration with the $2^{nd}$ IRP pitTSH and the $1^{st}$ IRP recTSH. In all instances, the recTSH preparation commercially used in this study was found immunologically similar to the IRP recTSH standard. For clarity and because the $2^{nd}$ IRP pitTSH is most often used in routine measurements, only this calibration has been given in the figures below.

Alternatively region I can be subdivided in regions Ia and Ib, which respectively recognized by pool Ia antibodies and pool Ib antibodies:
  pool Ia antibodies comprise: S04, B1, and BC27, and
  pool Ib antibodies comprise: B2, S09, and R1.

Example 2

I-Single Parameter Modification of the Glycosylation Pattern of the Glycoprotein Antigen The glycosylation pattern of recTSH was then modified, by either altering its sialylation state, its branching state or its fucosylation state.

It was then determined how the above-defined assays behave when they were given to bind the various preparations of TSH differing in glycosylation. The three sets of recTSH glycoforms were designed either by enzymatic reshaping to modify terminal glycosylation, lectin affinity chromatography for potential variation in branching (Con A chromatography) or core fucosylation (Lentil chromatography). A combination of the enzymatic and fractionation procedures addressed simultaneous changes in sialylation and core fucosylation as described for the onset of hypothyroidism.

I.1. Methods

The sialylation state of recTSH was modified by a neuraminidase treatment, which fully desialylated recTSH, followed by a sialyltransferase treatment by an engineered ST6Gal enzyme, to generate a serum-type sialylation of recTSH.

An oversialylated recTSH was also obtained by simply treating recTSH by the truncated form of a sialyltransferase without prior desialylation.

Briefly, the neuraminidase treatment was carried out as follows. 250 ng of recTSH was added to 250 µL neuraminidase buffer (100 mM sodium acetate, 2 mM $CaCl_2$, pH 6.5). Aliquots were incubated with or without 5 mU neuraminidase from *Clostridium perfringens* (Type X) at 30° C. overnight, under gentle stirring.

The preferred enzyme is a ST6Gal enzyme as no data in the literature showed a total coverage of glycoproteins with α2,6 linked sialic acid. Various secreted mutants of improved catalytic efficiency in transferring sialic acid in the α2,6 position have been obtained by deleting the N-terminal of hST6GalI to position 89 included and a stable CHO-K1 clone producing the soluble form of the Δ1-35 hST6GalI mutant enzyme has been previously characterized in vitro (Legaigneur, P., et al., 2001). Briefly, the cDNA encoding a truncated Δ1-35/89 form of human ST6GalI lacking the transmembrane segment was cloned into the pFLAG expression vector containing the preprotrypsinogen signal peptide. This form was stably transfected in CHO-K1 cells (Chinese Hamster Ovary cells). The CHO-K1/Δ1-35/89 hST6GalI cell line was grown in DMEM with Glutamax-I medium supplemented with 10% inactivated Foetal Calf Serum, fungizone (2.5 µg/mL), gentamycine (50 µg/mL), and geneticin (200 mg/mL) at 37° C. in a 5% $CO_2$ incubator. The cell culture medium was collected after a 72 h period and further concentrated >15-fold by Centriprep centrifugation. Batches were pooled and the soluble enzyme activity was standardized to a standard calibrator preparation (rat liver ST6Gal I) on asialofetuin as described by Legaigneur, P., et al. (2001). Under these conditions, concentrated supernatants were estimated to contain 0.06-0.1 mU/µL and aliquots were stored at −20° C. until use.

Sialylation of unsialylated recTSH (asialo-recTSH) was carried out in 96-wells microtiter plates. Briefly, the truncated form of hST6Gal I (1.2-2 mU) was added to different amounts of recTSH diluted in PBS containing 0.1% BSA, in a cacodylate buffer (50 mM cacodylate, 0.1% BSA, and 0.1% Triton X-100, pH 6.5) containing 0.9 µg CMP-NeuAc and 2 mM $MnCl_2$ in a final volume of 100 µL, and incubated over a 30 min-4 h period at 37° C. α2,6-linked sialic acid was measured by the sialic acid-specific lectin *Sambucus nigra* agglutinin (SNA) coupled to biotin as previously described (Legaigneur, P., et al., 2001). This modified glycoform of recTSH was named resialylated recTSH.

The extent of sialylation was followed by MALDI-TOF mass spectrometry analysis. Alternatively, α2,6-linked sialic acid was quantitatively measured in individual microtiter wells with 5 ng of the various TSHs by the use of the sialic acid-specific lectin *Sambucus nigra* agglutinin coupled to biotin as previously described (Legaigneur, P., et al., 2001). Streptavidin-alkaline phosphatase conjugate was used to amplify biotinylated SNA binding. Amplified complexes were revealed using p-NPP substrate. All the assays were performed in duplicates and the data are expressed as a mean of these values.

The ConA lectin (concanavalin A) was used to fractionate recTSH according to its branching state. Briefly, 0.5 mL of Con A-Sepharose was poured into a 3 mL disposable column and further equilibrated with 10 mL buffer containing 10 mM Tris-HCl, 150 mM NaCl, and 1 mM $MgCl_2$, $MnCl_2$, and $CaCl_2$ (pH 8.0) as described in Papandreou, M-J., et al., 1993. 5 µg of recTSH were loaded onto the column and allowed to interact with the lectin at least for 1 h at room temperature. Unbound recTSH was collected by 10 repeated centrifugations with 1 mL column buffer. Weakly bound and firmly bound fractions were collected using the same procedure and the same buffer with 10 mM α-methylglucopyranoside and with 500 mM α-methylmannopyranoside, respectively. PBS containing 2% BSA was added to stabilize fractionated material. Finally, recTSH concentration was determined by testing 100 µL of each fraction in solide-phase assay.

The Lentil lectin was used to fractionate recTSH according to its fucosylation state. The fractionation proceeded essentially as described for the ConA lectin except that the 10 mM α-methylglucopyranoside elution step was omitted.

Scale up for isolating oversialylated recTSH was carried out under batch conditions. Briefly, lectin gels were equilibrated with twice 5 mL of column buffer. 5-25 µg of oversialylated hormone was then mixed with the gel and allowed to interact with the lectin for 3 hr at room temperature under gentle stirring. The batch was then loaded onto the column and fractions collected as described above.

I.2. Results

Since measurements of TSH are routinely performed on plasma samples, it was of crucial importance to assess Ab recognition of TSHs that may mimic the glycoforms circulating in blood under normal and pathological conditions. Since sulfated TSH is short-lived (Szkudlinski, M. W., et al., 1995) while sialylated proved to be long-lived in the circulation, the behaviour of recTSHs, with a variable extent of sialylation towards the various formats described above, was first investigated.

To provide a sialylated source of recTSH very similar to plasma glycoproteins, the sialic acid content of the antigen was enzymatically modified by prior treatment by a neuraminidase and/or subsequent addition of α2,6-sialic acid by a recombinant sialyltransferase as described above. This glycosidic bond is not present in recTSH which only contains α2,3-sialic acid (Morelle, W., and Michalski, J-C., unpublished results). Antibody recognition was investigated by testing five different TSH glycoforms differing in sialylation: pitTSH, recTSH, asialo-recTSH, the so-called oversialylated-recTSH containing additive α2,6-sialic acid in addition to its α2,3-sialic acid content, and resialylated recTSH prepared from asialo-recTSH by adding only α2,6-linked sialic acid. All these glycoforms were assessed in the 6 formats defined above.

Figure 12A:
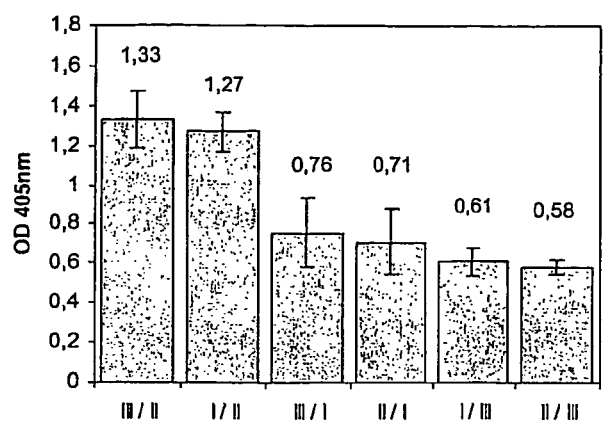
FIG. 12A, FIG. 12B and FIG. 12C
Figure 12B:
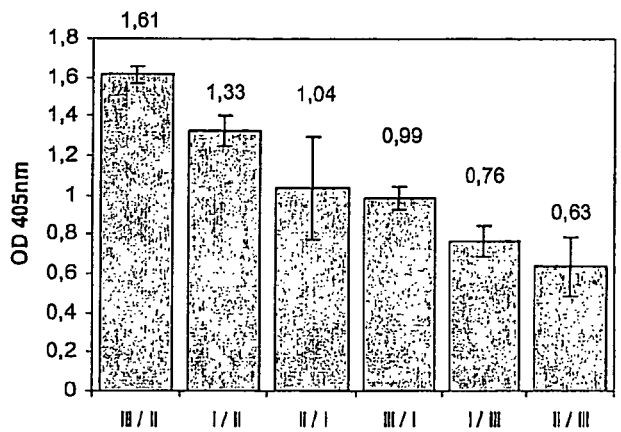
Figure 12C:
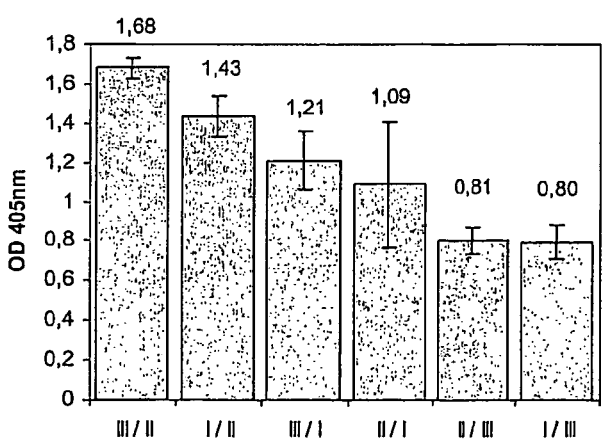
Figure 13A:
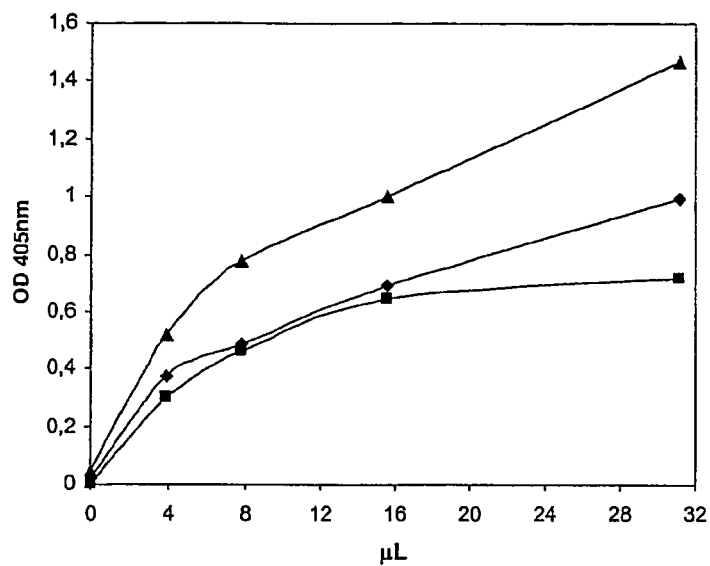
FIG. 13A and FIG. 13B
Figure 13B:
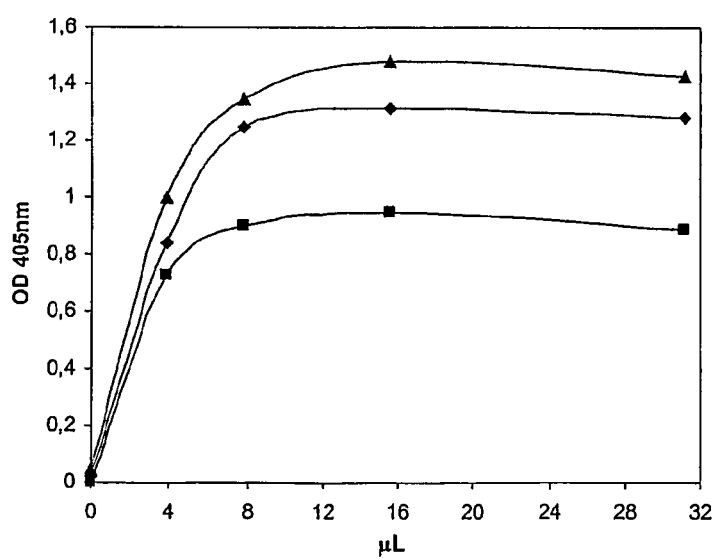

FIGS. 4A-E show the results of the 6 formats applied to IRP pitTSH, IRP recTSH and oversialylated recTSH and FIGS. 12A-C, summarize the plateau charge obtained for IRP pitTSH (FIG. 12A), IRP recTSH (FIG. 12B), and oversialylated recTSH (FIG. 12C with the various formats. In all formats, the recognition of asialo-recTSH was virtually identical to recTSH and for sale of clarity has not been included in FIG. 12.

Figure 16A:
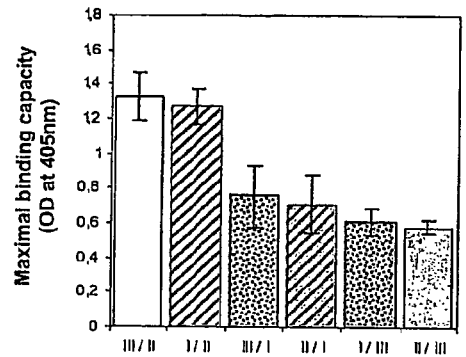
FIG. 16A, FIG. 16B, FIG. 16C, FIG. 16D, FIG. 16E, and FIG. 16F
Figure 16D:
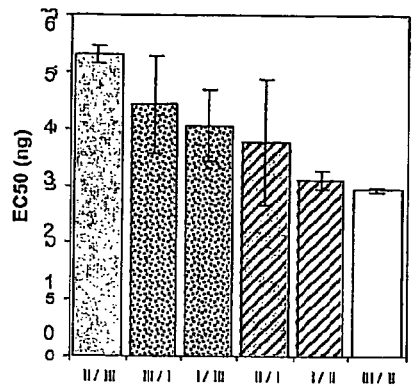
Figure 16B:
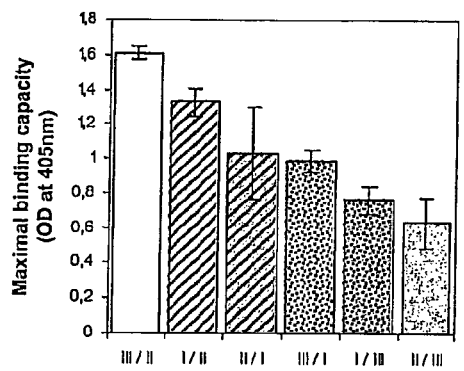
Figure 16E:
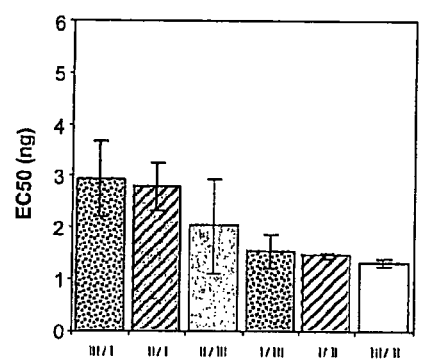
Figure 16C:
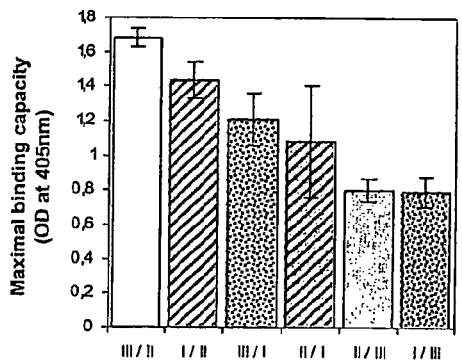
Figure 16F:
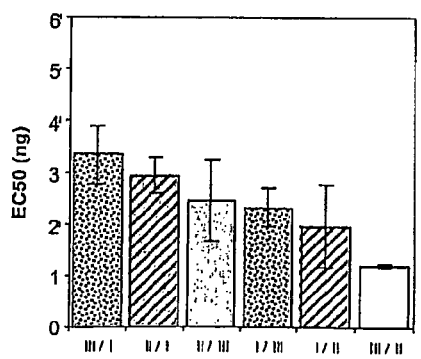

When these preparations were estimated with an ultrasensitive amino acid assay, no significant difference was observed in estimating the dose-response curve of each standard preparation (data not shown), suggesting that no artefact of protein quantitation has been introduced. 1 mL of diluted albumin (BSA) standards and unknown sample were mixed with 1 mL of the Working Reagent provided by the manufacturer, and incubated at 60° C. in a water bath for 1 hr. The Working reagent contains bicinchoninic acid (BCA) as the detection reagent for Cu+, which is formed when Cu++ is reduced by protein in alkaline environment. This water-soluble complex exhibits absorbance at 562 nm that is linear with increasing protein concentration. After cooling all tubes to room temperature, OD at 562 nm was measured FIGS. 16A-16F summarize the maximal binding capacity of the various formats, with respect to IRP pitTSH (FIG. 16A), IRP recTSH (FIG. 16B), and oversialylated recTSH (FIG. 16C) and their corresponding EC50 in FIGS. 5D-F respectively. When pitTSH is considered, a group of 2 assays (III/II and I/II) displayed a binding capacity twice that of the others (FIG. 16A), indicating that some mAbs fail to several bind pitTSH forms. Since the II-III as well as I-II formats showed variable binding efficiency when the antibodies were alterned, it was concluded that epitope II is likely to be conformational and better targeted by the tracer antibody. When recTSHs were investigated as a function of their extent in sialylation, the overall binding of TSH was increased (FIGS. 16B-16C) confirming that most mAbs exhibit a potential preference for sialylated forms. Turning to the EC50, a 2- to 3-fold decrease was observed for recTSH (FIG. 16E) compared to pitTSH (FIG. 16D). The half-maximal binding of the assays did not correlate with their binding capacity except for the III/II assay which showed the lowest EC50 for the largest binding capacity. No further difference was observed as a result of oversialylation (FIGS. 16E-16F). These data indicated that the assays were discriminating TSH subforms as a function of their concentration in the various preparations.

Figure 5A:
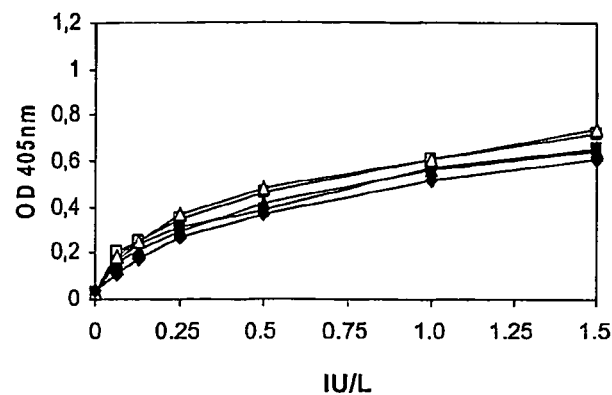
FIG. 5A, FIG. 5B and FIG. 5C

The S06/BC27 pairing (format III/I) displayed an equal binding of TSH glycoforms similar to $2^{nd}$ IRP pitTSH and was thus found sialylation-independent (FIG. 5A). This finding is in good agreement with the observation that the I-III format exhibited the lowest efficiency in binding sialylated TSHs (FIGS. 16C-16D). Other formats based on tracer antibodies targeting epitope I behaved very similarly indicating that the Main Immunogenic Region (MIR) is not significantly affected by such altered glycosylation. This indicates that these formats bind and estimate glycoforms expressing the same epitope as in the pituitary IRP standard, independently of changes in terminal glycosylation.

Figure 5B:
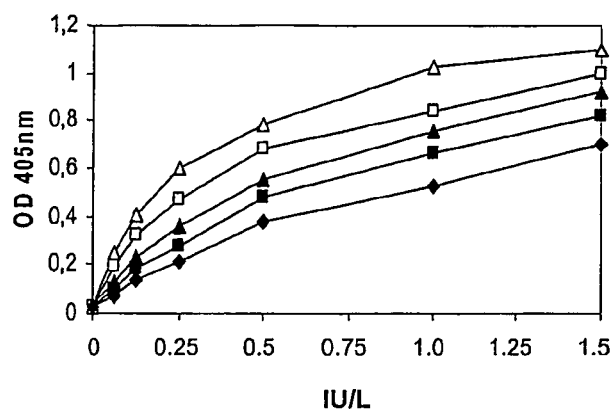
Figure 5C:
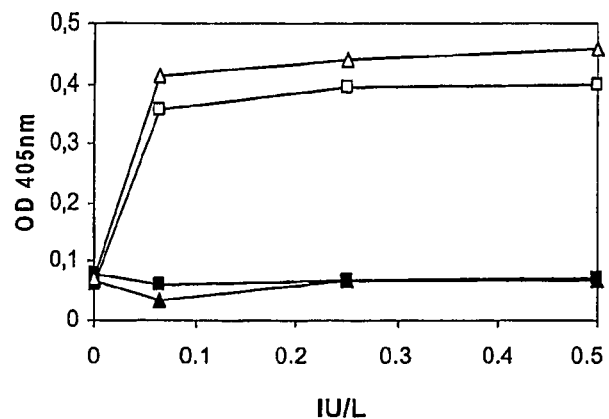

In contrast, testing the BC27/OCD1 pairing (format I/II) revealed higher binding of sialylated TSH glycoforms, and thus exhibited a typical sialylation-dependent behaviour (FIG. 5B). An increased binding with antigen further modified by α2,6-sialylation compared to the α2,3 linked sialic acid was also evidenced. The presence of α2,6-linked sialic acid in oversialylated glycoforms added by the recombinant α2,6-sialyltransferase was controlled by SNA binding (FIG. 5C) and mass spectrometry (data not shown).

Figure 6A:
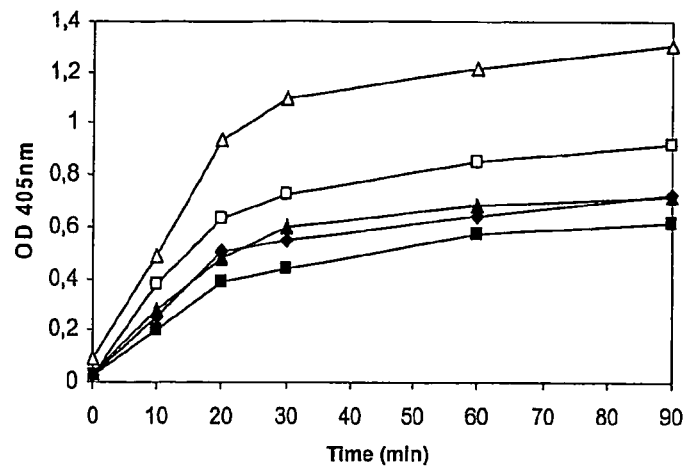
FIG. 6A and FIG. 6B
Figure 6B:
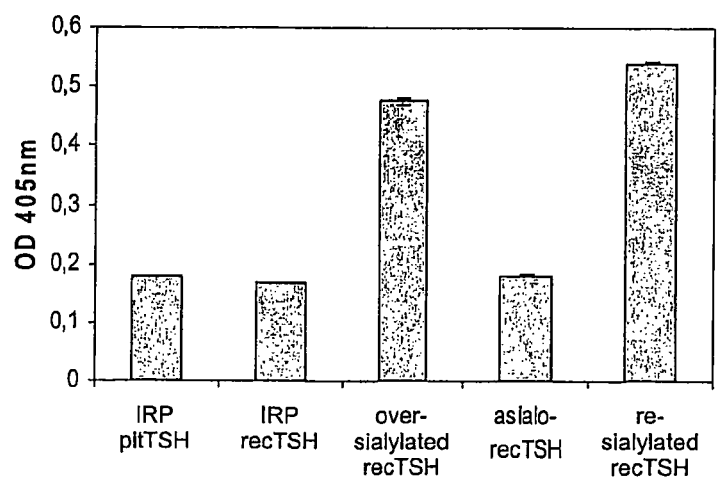

To better understand the basis of such an increase in antibody binding, antibody recognition was analyzed as a function of time (FIG. 6A) and the data obtained with the BC27/OCD1 pairing were confirmed with the tracer antibody i.e. that recognition of mAb OCD1 heavily relies on the presence of sialic acid. The contents in α2,6-linked sialic acid for the enzymatically engineered glycoforms were also controlled and an enhanced signal after α2,6-sialylation (FIG. 6B) was detected, indicating that both the oversialylated and resialylated TSHs reached virtual completion in sialic acid as previously reported (Legaigneur et al., 2001). This demonstrated that increasing the extent of sialylation in TSH allowed a better recognition of the array of TSH glycoforms: virtually, antibody binding to resialylated TSH is 2-fold that of the pitTSH calibrant at equilibrium. This also suggested that among glycoforms, some lack antibody recognition because epitope II is poorly expressed as a result of a low content in sialic acid.

These experiments demonstrated that using a format equally efficient in binding pitTSH and recTSH may result to a 100% lower binding compared to an assay capable to bind sialylated TSH. Since most circulating forms to be measured in blood were previously demonstrated to be enriched in sialic acid, these data therefore strengthen the importance of having a sialylated calibrator for measuring plasma TSH level under most pathophysiological circumstances. At present, pituitary extracts are most often used for calibrating commercial kits because no plasma TSH can be isolated in sufficient amount from blood. As a result, the current calibrator is not representative of the circulating antigen to be measured. Under these conditions, TSH level is likely to be overestimated as the nature of its glycosylation significantly differs from the pituitary antigen, especially in primary hypothyroidism.

To further investigate what level of glycan heterogeneity may affect TSH immunodetection and possibly deduce what could be the best match between the antibodies and the calibrant, fractions of recTSH, the glycosylation state of which differed, were isolated by affinity chromatography on lectins. This well established chromatography is known to discriminate glycans according to their degree of branching for ConA fractions or their content in inner fucose for the Lentil fractions. Each fraction is supposed to share common structural features but can still contain terminal microheterogeneity. Sialylation does not affect the isolation.

N-glycans are widely considered as possessing inner microheterogeneity as most glycoproteins exist with and without core fucosylated glycans. This modification is believed to be independent of the degree of branching and of terminal glycosylation, although TSHs that bound firmly to ConA also tended to bind firmly to lentil (Miura, Y., et al., 1989). Core fucosylation is largely admitted to increase the hydrophobicity of the core pentasaccharide by modifying the orientation of the α-1,6 arm and thus the steric occupancy of the whole glycan (Unverzagt, C., et al., 2002). It is also known to increase the metabolic clearance of plasma glycoproteins by liver.

Primary hypothyroid TSH has been reported to have a reduced core fucosylation compared to the euthyroid state (Schaaf, L., et al., 1995). recTSH was therefore fractionated on a lentil column which specifically binds fucosylated glycoproteins and the effect of inner glycan alteration were analyzed in our 6 assays. To closely mimic the situation found in plasma, recTSH was oversialylated before affinity chromatography and the unbound and bound fractions were measured based on assay calibrated with recTSH on a molar basis. Of note, the unbound fraction is highly homogeneous in that the hormone contained unfucosylated glycans at the three N-glycosylation sites.

Figure 7A:
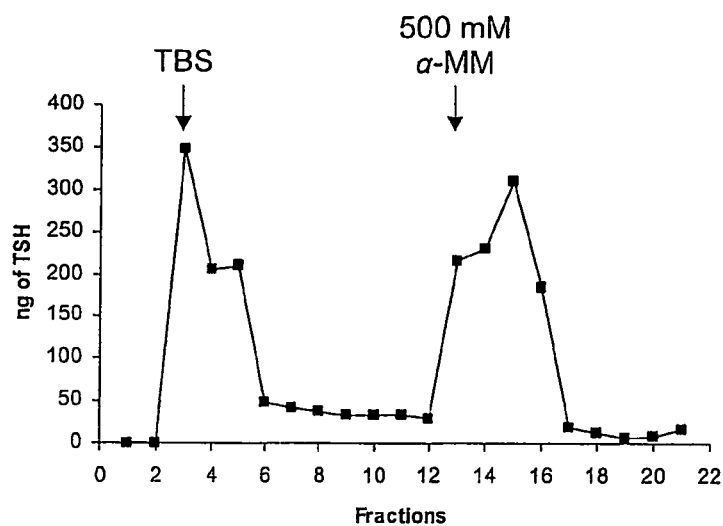
FIG. 7A and FIG. 7B

Lentil-lectin affinity chromatography showed that 48.4±3.3% (±SD) of recTSH glycoforms contained no fucose residue and 51.6±3.3% had at least one internal fucose among the three N-glycans present on the molecule (FIG. 7A and Table II). This allowed us to isolate lentil-unbound (L-UB) fractions (not fucosylated) and lentil-bound (L-B) fractions (with fucose).

Figure 17:
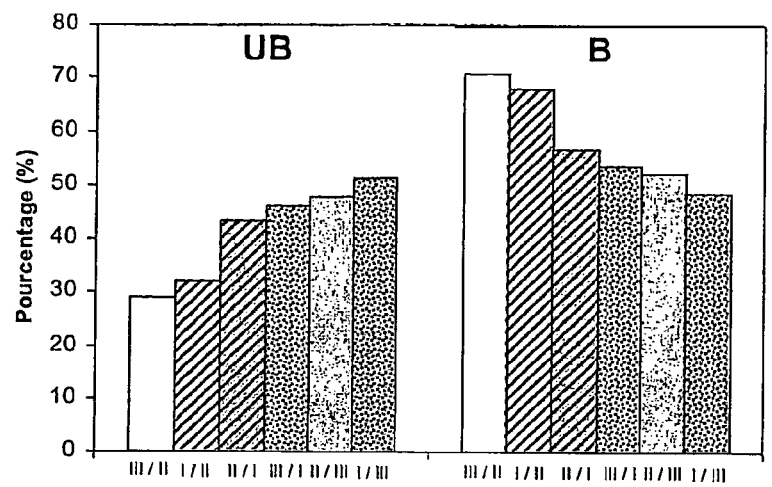
FIG. 17

FIG. 17 further shows that under equilibrium conditions, the lentil-unbound and -bound fractions displayed distinct immunological behavior when tested simultaneously in the whole combination of assay. The I/III assay estimated a virtually even distribution of TSH (49% UB-51% B) between the two fractions. In contrast, the III/II assay exhibited almost twice this binding for the bound fraction (29% UB-71% B). Since the compound was fully sialylated, it appeared that most sialylated forms are retained on the lentil column. As observed above, such sialylated glycoforms are better recognized when using formats including the recognition of epitope II. In contrast, formats targeting epitope III were less efficient in binding fucosylated TSH, whereas formats binding epitope I had broader recognition. These findings indicated that both epitopes I and III may be differently expressed as a function of the fucose content in TSH.

Plasma TSH in euthyroid subjects and hypothyroid patients has been shown to exhibit a different pattern on Con A chromatography compared to pituitary TSH as a higher content in Con A-UB fraction was observed (Papandreou, M. J., et al., 1993). This finding was interpretated as a higher degree of branching in TSH glycans. To determine if this alteration may affect recognition of TSHs, sialylated recTSH was fractionated by Con A chromatography and the binding distribution of the three fractions was analyzed in the 6 assays at equilibrium.

Figure 7B:
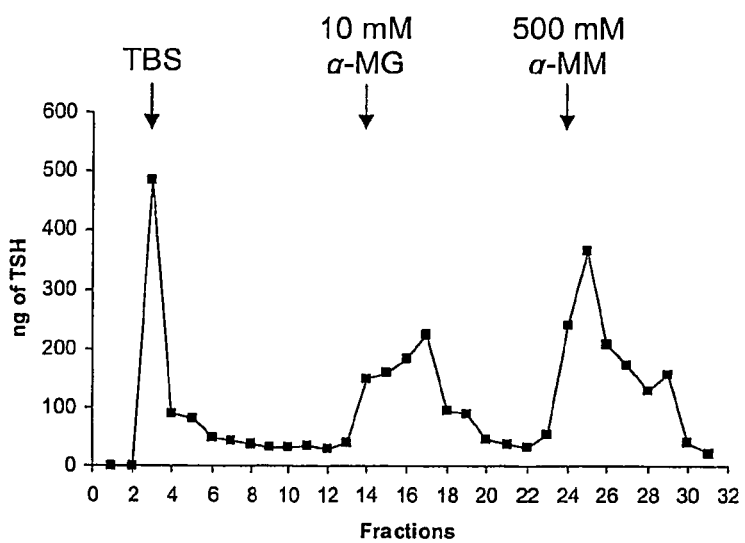

Alternatively, binding of recTSH to the Con A column was distributed in three fractions: unbound, weakly bound and firmly bound (FIG. 7B and Table II). Most recombinant TSHs were retained on Con A [unbound, 15.7±5.9% (±SD); weakly bound, 29.1±2.9%; firmly bound, 55.2±7.6%]. The three fractions were designed as Con A-Unbound (UB), weakly bound (WB) and firmly bound (FB). As in FIGS. 5 and 6, all assays were calibrated with the $2^{nd}$ IRP pitTSH and $1^{st}$ IRP recTSH standards.

Figure 18:
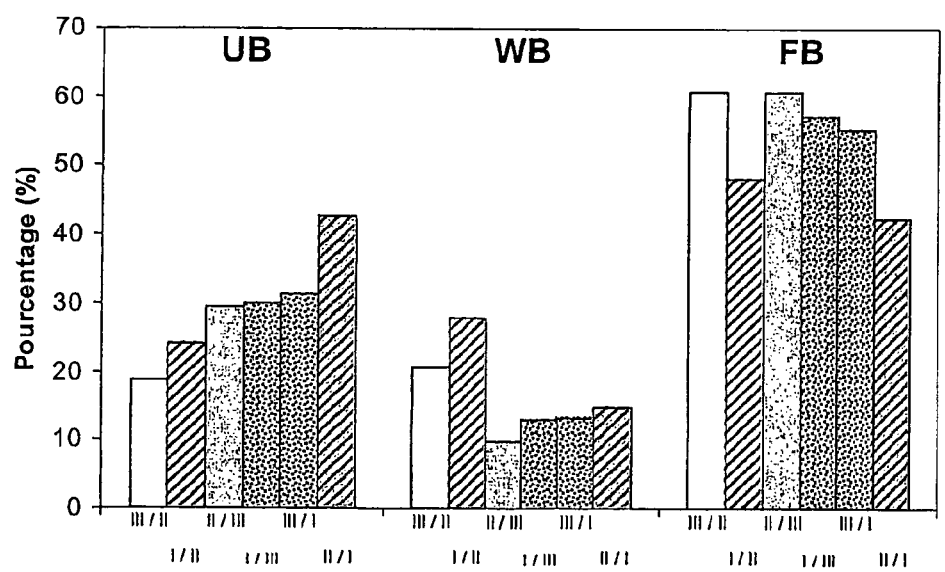
FIG. 18

FIG. 18 further shows that the UB, WB and FB fractions were unevenly estimated when tested in parallel in the various assays. When each fraction was quantitated against recTSH on a molar basis, the UB fraction was ranging from 19% to 43%, while the WB fraction was about 10-28% and the FB fractions from 48-61%. Of interest, a mean value of 18-21-61% as estimated with the III/II assay is similar to a 11-37-52% distribution described earlier for primary hypothyroidism (Miura, Y., et al., 1989) while that of 24-28-48% measured by the I/II assay is in reasonable agreement with the 27-34-38% distribution reported for euthyroid subject (Papandreou, M. J., et al., 1993), indicating that recTSH may satisfactorily reproduce the heterogeneity of circulating TSH. Since TSH circulating in euthyroid patients may display increased sialic acid content, and the one found in hypothyroid patients may combine increased sialylation with decreased fucosylation, it is not surprising that III/II and I/II assays closely approach the distribution obtained with hypothyroid and euthyroid TSH respectively. Indeed epitope II best allows to target sialylated glycoforms and epitope III non fucosylated glycoforms.

TABLE II

Isolation of recTSH fractions based on lectin chromatography:

| Lectin-chromatography | Fractions | |
|---|---|---|
| Lentil | L-UB | 48.4 ± 3.3% |
| | L-B | 51.6 ± 3.3% |
| ConA | ConA-UB | 15.7 ± 5.9% |
| | ConA-WB | 29.1 ± 2.9% |
| | ConA-FB | 55.2 ± 7.6% |

Results are expressed in % and determined with the S06-BC27 assay.

To study the influence of inner fucosylation, we compared the behaviour of mAbs with fucosylated and non fucosylated TSHs separated by Lentil chromatography to the whole preparation of recTSH and in format calibrated with IRP pitTSH.

Figure 8A:
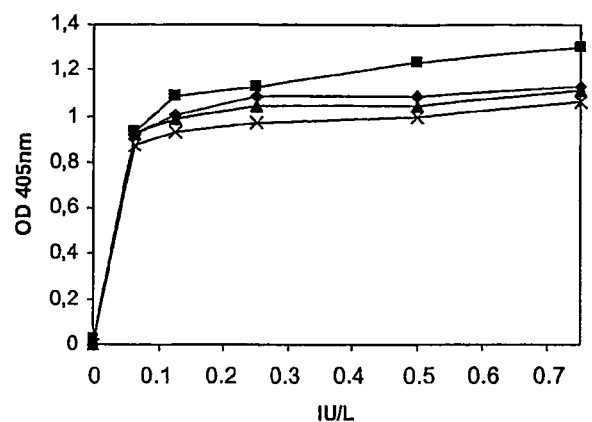
FIG. 8A and FIG. 8B
Figure 8B:
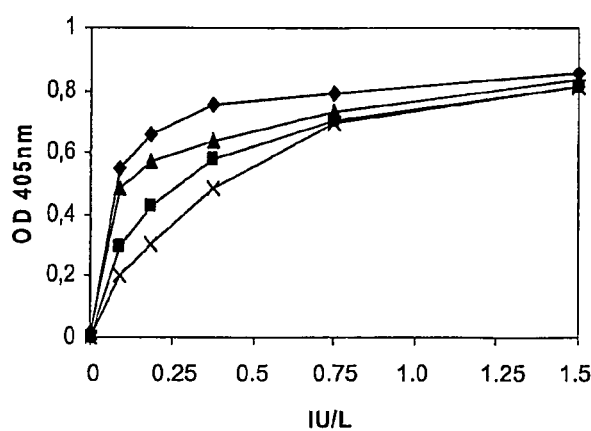

The use of the BC27/OCD1 pairing (format I/II) revealed a binding of L-UB and L-B fractions very similar to the crude preparation and pitTSH standard, in that it poorly recognizes the fucosylated forms (FIG. 8A). In contrast, S06/S04 pairing (format III/I) displayed not only a higher binding of than the IRP standard with an improved recognition of fucosylated glycoforms (FIG. 8B). A two-fold difference was observed at the $EC_{50}$, indicating that inner fucosylation increased Ab recognition. It was concluded that this sandwich was not dependent on TSH fucosylation in contrast to the I/II format.

To identify which epitope was fucosylation-dependent, we carried out the kinetics of binding of the capture (mAbs S06) and tracer (mAb S04) antibodies independently. S06 binding was found to display variable binding to the various TSHs upon time whereas mAb S04 showed no discrimination towards the fucose content of TSH glycoforms (FIG. 9). This allowed us to assign epitope III as being under the control of core fucosylation. It is conceivable that increasing inner fucosylation in TSH may alter expression of this epitope since the content of the recombinant product is high. This also opens the possibility that under primary hypothyroidism, increasing fucosylation of blood TSH may alter TSH measurements progressively depending on the antibodies used in the assay and results in discordant measurements among kits which contain different combination of Abs.

Figure 9A:
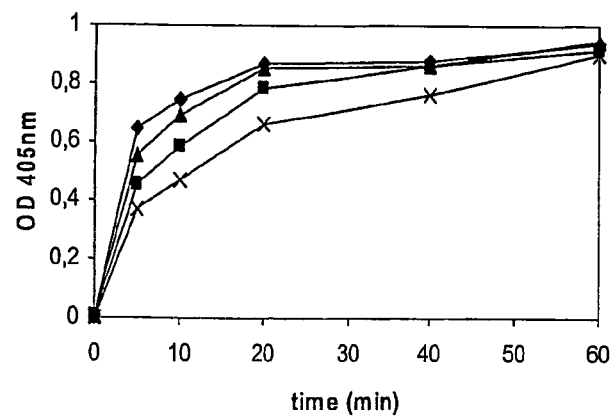
FIG. 9A and FIG. 9B
Figure 9B:
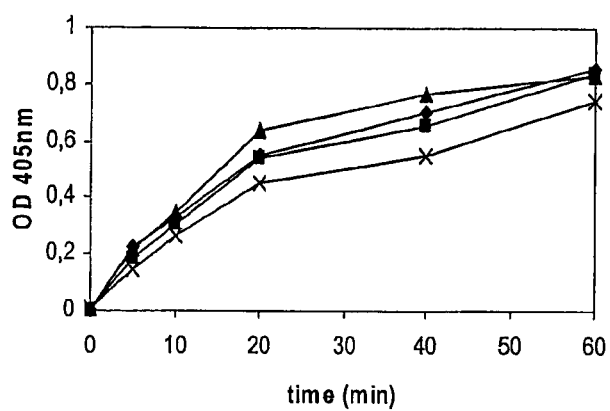

To identify how antibody recognition may depend on TSH core fucosylation, binding experiments were conducted within shorter periods of time and at low concentration of unmodified recTSHs to avoid a potential interference with the content in sialic acid (FIGS. 8A-8B, 9A-9B). The I/II assay showed no major difference in binding among lentil fractions, recTSH and pitTSH (FIG. 8A), indicating that in this case, the presence of inner fucose in the analyte does not significantly affect TSH measurement. FIG. 8B however shows a 3-fold increase in the recognition of the UB lentil fraction over pitTSH in the III/I assay. To determine which of the epitope I or III was responsible for this variation, we carried out kinetics studies at low TSH concentration. As shown in FIG. 9A, binding of mAb (S06) targeting epitope III exhibited an increased recognition for both lentil fractions compared to pitTSH under limiting concentration of antigen. In contrast, binding of mAb (S04) recognizing epitope I was unaffected (FIG. 9B). In both instances, optimal binding was reached within 60 min. This indicated that in TSH, expression of epitope I is likely to be independent of core fucosylation. As a result, a decrease in inner TSH glycosylation will not affect the measurement of hormone level as primary hypothyroidism develops provided that mAbs are directed against epitope I. Conversely, recognition of epitope III of non fucosylated recTSH was found to be faster than the fucosylated fraction or any of the total TSHs, indicating a higher affinity of the antibodies. As a result, disease-related TSH may compete with increased secretion of many other altered glycoforms within a short period of time if epitope III were to be targeted by capture antibodies. The measurement may then be overestimated by a factor of 3-5 when using a pituitary calibrator, especially at low level of TSH (FIG. 8B).

Since plasma TSH was observed to be largely unretained on ConA chromatography compared to pitTSH standard under normal or pathological conditions (Papandreou, M-J., et al., 1993), the Inventors also paid special attention to the binding of antibodies towards TSHs isolated by this lectin.

Like in the experiments described above, the three TSH fractions against all the formats calibrated against the 2$^{nd}$ IRP pitTSH were tested. In most instances, the respective distribution among Ubd vs WB vs FB fractions was differentially estimated by the various formats while the total recovery was similar. As shown in FIGS. 10A-10D, no difference in dose-dependent binding among the 3 TSH fractions could be noticed among 4 formats, with most of them displaying a significant increase in binding capacity compared to the pitTSH standard. It can be concluded that branching per se does not significantly influence the recognition of any of the 3 epitopes. These data nevertheless further support the proposal that a combination of certain antibodies allowed better binding than others depending on the calibrant used.

Figure 10A:
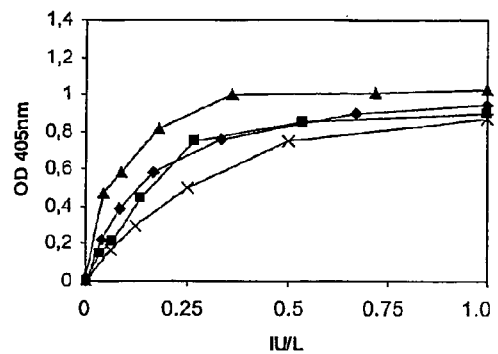
FIG. 10A, FIG. 10B, FIG. 10C and FIG. 10D
Figure 10B:
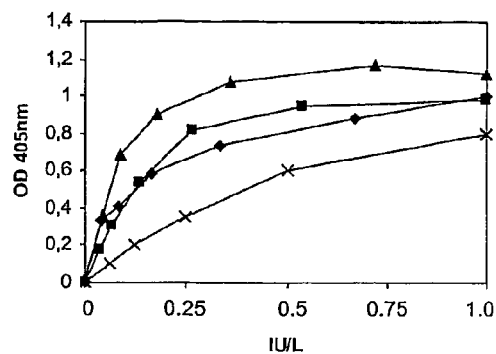
Figure 10C:
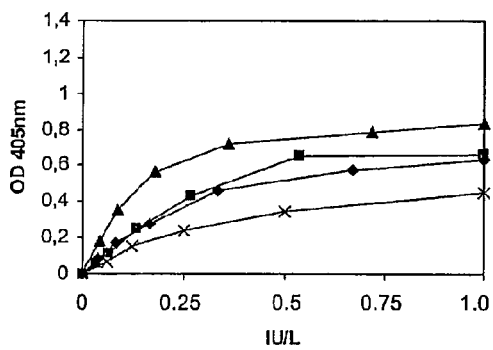
Figure 10D:
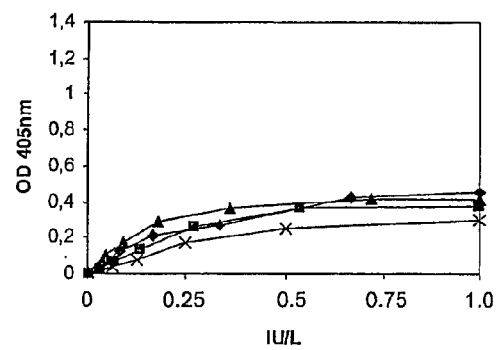

FIGS. 10A-10D shows that in the absence of resialylation and at equilibrium, there was a major variation in antibody recognition not so much among the three Con A fractions but rather with respect to the pituitary standard (FIGS. 10A-10C) except for the I/III assay which displayed the lowest capacity (FIG. 10D). Like the I/II (FIG. 10A) and the III/I (FIG. 10C) assays, the III/II assay exhibited an increased recognition of Con A fractions of recTSH but no major difference in binding capacity among assays (FIG. 10B). The FB fraction appeared best recognized in all assays. The glycan structure of this so-called FB material was thus analyzed by mass spectrometry to get an insight of this abundant fraction but no peculiar glycan structure could be attributed to this fraction.

Since the Con A-UB fraction may be of physiological relevance, the Inventors focused on this fraction in spite of a limited amount which precluded structural characterization. Preliminary work revealed that ConA-UB fraction of sialylated recTSH is also unbound on a Lentil column. This fraction should presumably contain highly complex nonfucosylated glycans at all N-glycosylation sites and is likely to combine the most dramatic changes in epitope expression. Indeed a significant increase of epitope III expression may very well occur as the fucose content is diminished while the epitope I expression is unchanged and epitope II even gained as the content in sialic acid increases. The estimation of ConA-UB fraction by most formats appeared quite variable. At the EC50, such TSH glycoforms may be overestimated by a factor of 8 by the III/I assay, by a factor of 6 with a III/II assay or by a factor of 5 by the I/II assay when they are measured against pitTSH. It is worth noticing once again, that the amount of unknown entities may be dramatically overestimated within the low concentration range.

As a result, it is proposed that the choice of epitope for the capture antibody should be associated with the use of the calibrant, both being critical for the final measurement of TSH (FIGS. 12A-12C). Then, the choice of a given tracer antibody will further improve the overall quantitation depending whether or not it recognizes an epitope under the control of sialylation. Basically 3 groups of formats can be designed:

1-Formats I/III or III/I:

The MIR determinant can be used to capture glycoforms sharing the highest similarity with pitTSH (glycoprotein 1). Because this latter is recognized by most of the antibodies commercially available, epitope I offers a variety of possibilities for commercial use to construct formats which are poorly sensitive to changes in glycosylation. Epitope III (format I/III) is acceptable to be used as tracer epitope in that it fully accommodates changes in fucosylation. This sandwich format will be best calibrated with pitTSH and other unsialylated/poorly sialylated and poorly fucosylated glycoforms of pit/recTSH like Lentil-unbound fractions.

2-Formats I/II:

Epitope II (format I/II) allows a definite better recognition of TSHs enriched in sialic acid. It should be used in conjunction with a sialylated calibrant to allow satisfactory estimation, especially at low levels of TSH.

When associated to a capture antibody directed against epitope I, the calibrant should also contain a low content in core fucosylation to approach a quantitative measurement of the antigen. As a result the best calibrant would be the Lentil-unbound fraction of over/resialylated recTSH.

3-Formats III/II:

Selecting antibodies targeting epitope III definitely permits to capture the highest amount of glycoforms independently of the nature of the calibrant (pitTSH vs. recTSH) and of the extent of sialylation of the sample measured (recTSH vs. oversialylated recTSH). Using epitope II further increases the maximal binding capacity of the assay. The best estimation will be provided by using a highly sialylated and highly fucosylated calibrant like the Lentil-bound fraction of over/resialylated recTSH.

Since the expression of the 3 relevant epitopes are each under a differential control of TSH glycosylation state, the above proposal is also intended to solve the discordances observed so far among TSH measurements. To allow satisfactory detection of altered TSH enriched in sialic acid and fucose, epitope III will be better used as capter epitope to optimize binding of fucosylated TSHs upon the onset of hypothyroidism. Epitope II as tracer to allow the highest detection of all the forms for which the extent of sialylation has been increased as the disease develops. Since the alteration of TSH glycosylation in the whole panel of thyroid disorders is still unknown, this format appears also best suited for the diagnostic and the follow up of these diseases.

Example 3

Multiple Parameter Modification of the Glycosylation Pattern

So as to obtain glycoforms of recTSH for which two or more of the glycosylation parameters are altered, successive modifications of recTSH were carried out by enzymatic treatment and/or chromatographic fractionation, according to the methods already described.

Figure 11A:
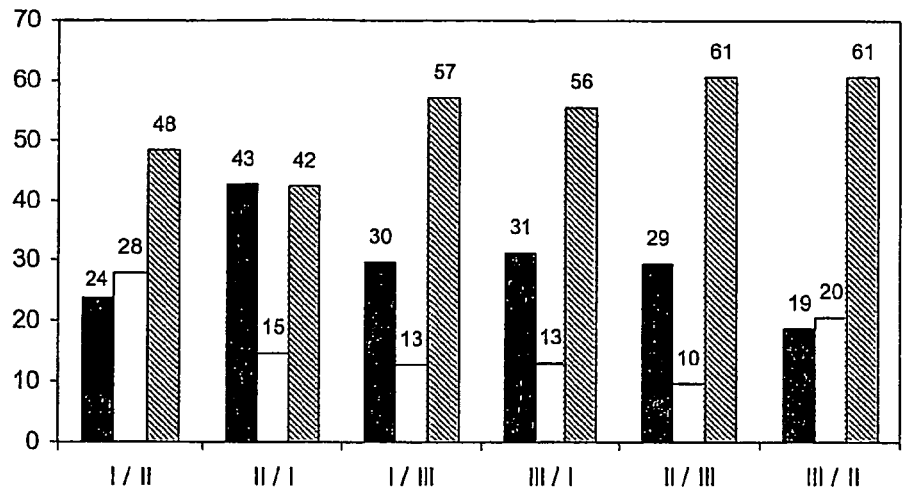
FIG. 11A and FIG. 11B

In a first instance, oversialylation of recTSH followed by ConA chromatography was performed. The results of the various immunoassays formats according to the invention are shown in FIG. 11A.

Figure 11B:
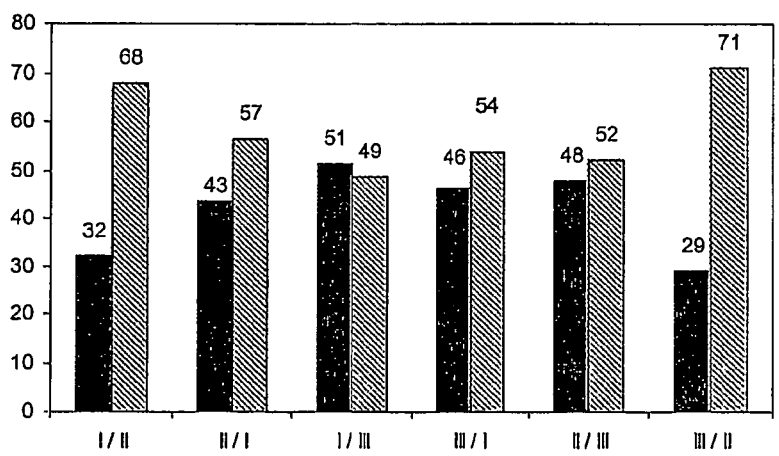

In another instance, oversialylation of recTSH followed by lentil chromatography was performed. The results obtained for the various immunoassays formats according to the invention are shown in FIG. 11B.

In still another instance, sialylation was first performed on recTSH, followed by a ConA chromatography and then by a lentil chromatography of the ConA unbound fraction. Our results showed that the oversialylated ConA unbound fraction is not retained on lentil.

Example 4

Selection of Antibodies Directed Against a Recombinant TSH

Any of the recombinant TSH preparation or fraction used in the preceding examples can be administered to mice in order to produce several monoclonal antibodies specific for TSH according to the general procedure described by Kohler, G., and Milstein, C. (1975).

The anti-TSH monoclonal antibodies can then be screened against any of the glycoforms of any recTSH fractions or preparations described in Examples 2 and 3.

Several antibodies are obtained which preferentially recognize either the oversialylated or the resialylated glycoforms of recTSH as compared to recTSH itself. Those antibodies are useful for the detection of the putative forms of TSH circulating in blood of hypothyroid patients, patients with non-thyroid illnesses, or TRH-treated patients. Such forms contain highly branched and sialylated chains as reported in Papandreou et al., 1993. Occasionally, as for hypothyroid TSH, they also have altered core fucosylation. Such disease-related glycoforms are best measured with the III/II format calibrated with enzymatically resialylated recTSH fractions. In contrast, low or subnormal TSH levels, as in euthyroid subjects, are better estimated by glycosylation-independent formats calibrated with either pitTSH or recTSH such as the I/III or II/I format Preferably, the I/II format may show a lower sensitivity threshold, provided that binding properties of the antibodies and calibration with pit/recTSH are further optimized better suited for daily use of these assays which may be quite far from equilibrium.

Example 5

Immunological Comparison of Pituitary, Recombinant, and Plasma TSH

The epitopic cartography of plasma TSH was performed on serum samples of hypothyroid individuals (plasma concentration above 100 mIU/L) by using the above mentioned formats corresponding to epitopes Ia, Ib, II and III. Thus, 45 antibody combinations were used (5 tracer antibodies and 9 capture antibodies).

A quantity of antigen close to the EC50 was used (2 ng) so as to operate at half the binding capacity of the assay formats. The value retained for antigen binding was that reached at equilibrium.

A comparative epitopic cartography of pitTSH and recTSH was also performed in the same conditions, with rabbit serum or hyperthyroid serum so as to disregard the effect of the serum in plasma TSH samples.

Figure 19A:
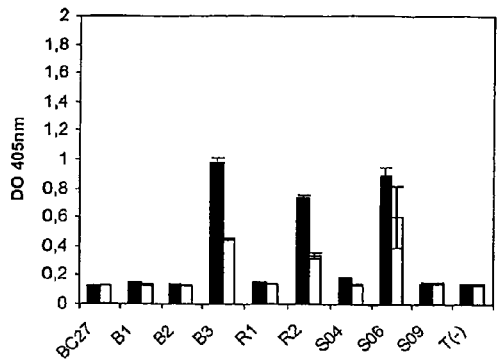
FIG. 19A, FIG. 19B, FIG. 19C, FIG. 19D, FIG. 19E, FIG. 19F, FIG. 19G, FIG. 19H, FIG. 19I, FIG. 19J, FIG. 19K, FIG. 19L, FIG. 19M, FIG. 19N, and FIG. 19O FIGS. 19A to 19F represent the quantitative epitope oriented mapping of pituitary, recombinant and blood TSH using tracer antibodies directed against epitope I.
Figure 19B:
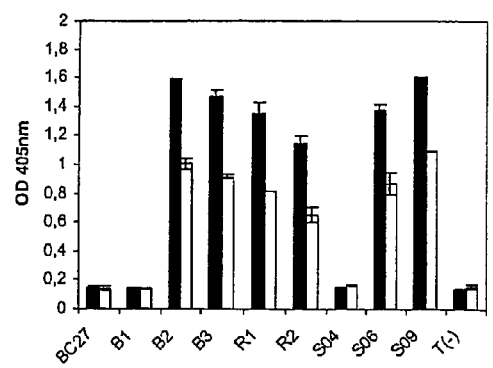
Figure 19C:
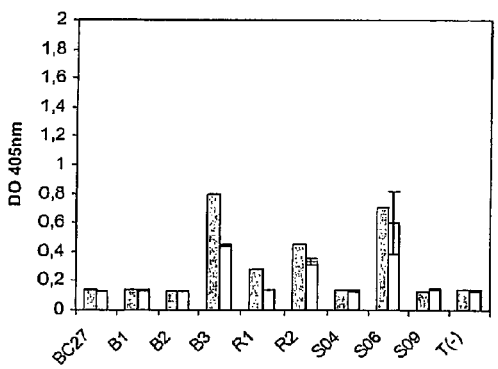
Figure 19D:
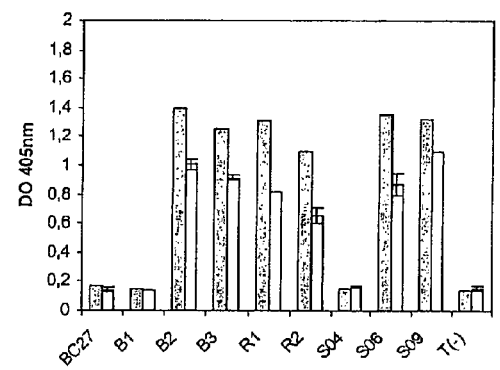
Figure 19E:
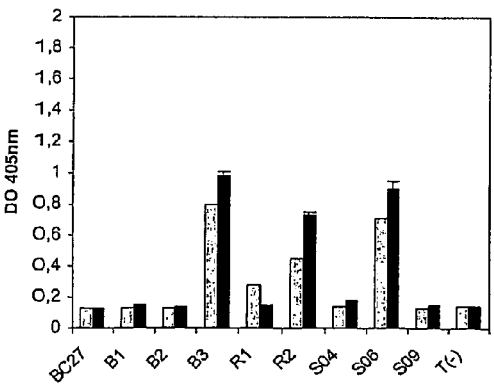
Figure 19F:
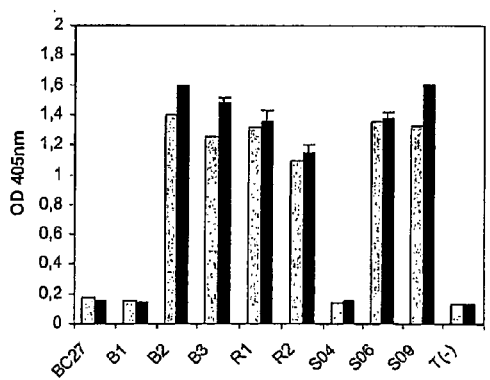
Figure 19G:
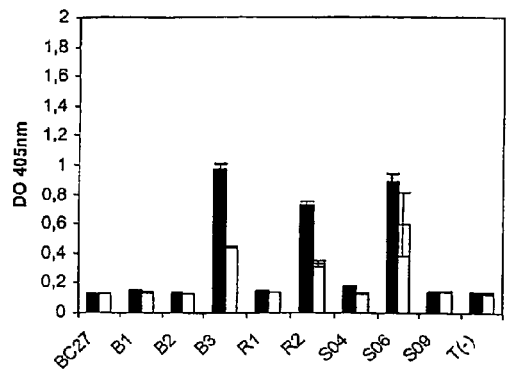
Figure 19H:
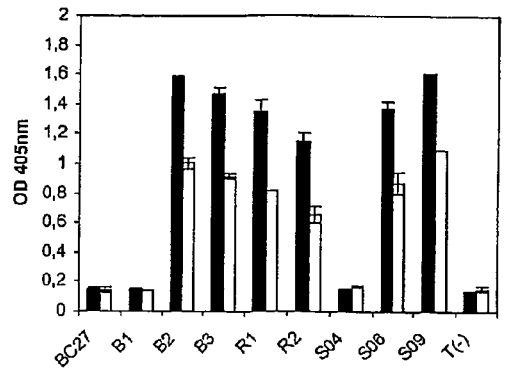
Figure 19I:
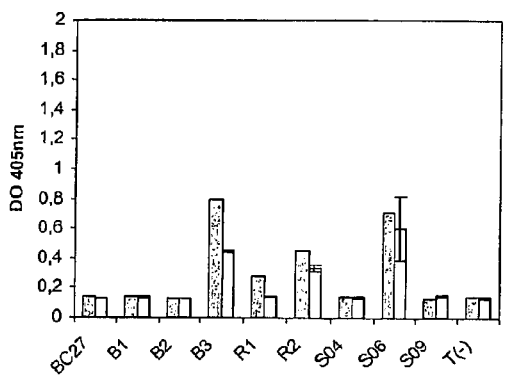
Figure 19J:
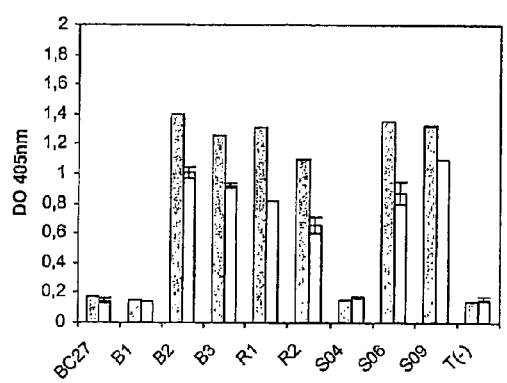
Figure 19K:
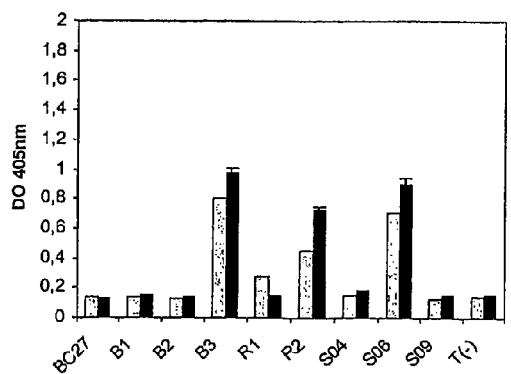
Figure 19L:
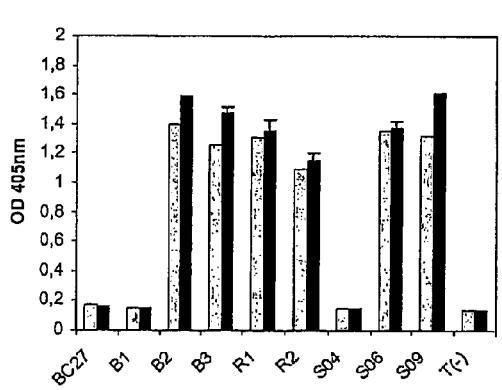
Figure 19M:
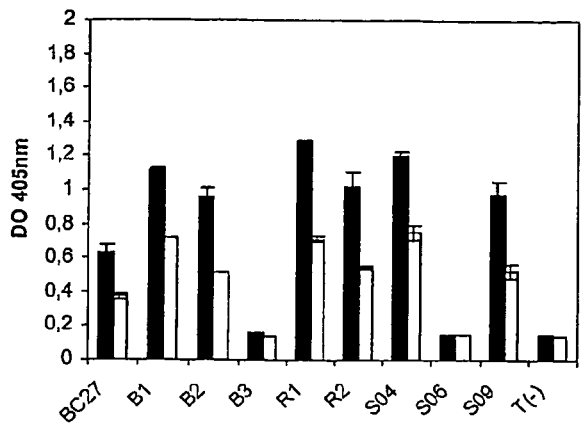
Figure 19N:
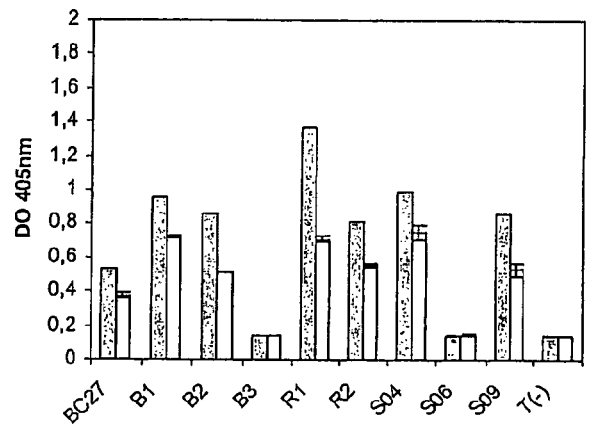
Figure 19O:
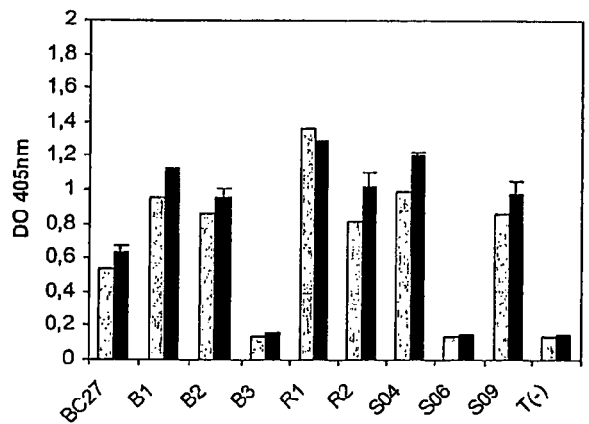

The results are shown in FIGS. 19A-19O.

Overall, these results are coherent with the results obtained in the previous Examples with saturating concentrations of the antigen, that is a higher binding capacity of recTSH with respect to pitTSH.

Plasma TSH shows an overall binding stronger than that of pitTSH and equivalent (epitope I and III) or identical (epitope II) to that of recTSH. Moreover, antibody R2 binds more strongly to plasma TSH than to pit TSH and recTSH.

Of note, formats with tracer antibodies directed against epitope II have the highest binding capacity. This is not surprising given that this epitope is sialylation-dependant and that hypothyroid conditions are characterized by an increase in sialic acid levels. Thus, this epitope is of great importance for detecting hypothyroidism onset.

Figure 20A:
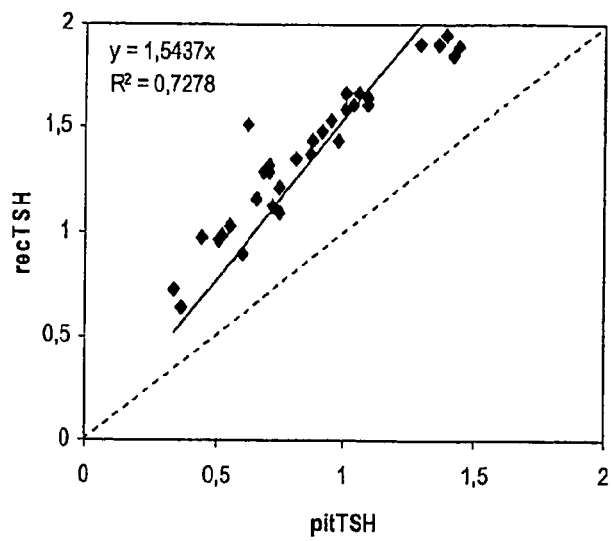
FIG. 20A, FIG. 20B and FIG. 20C
Figure 20B:
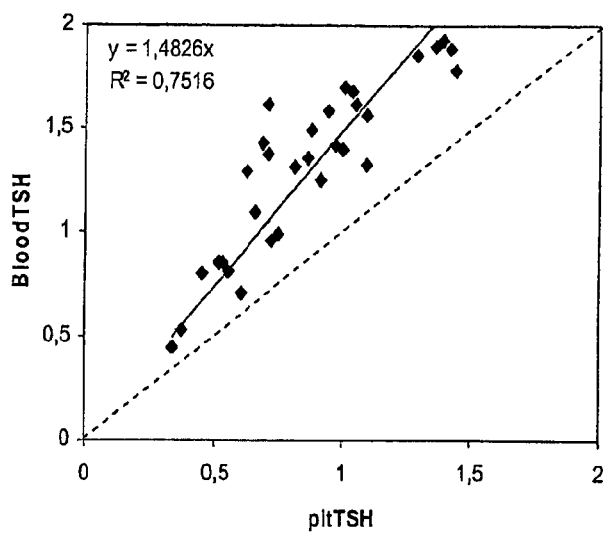
Figure 20C:
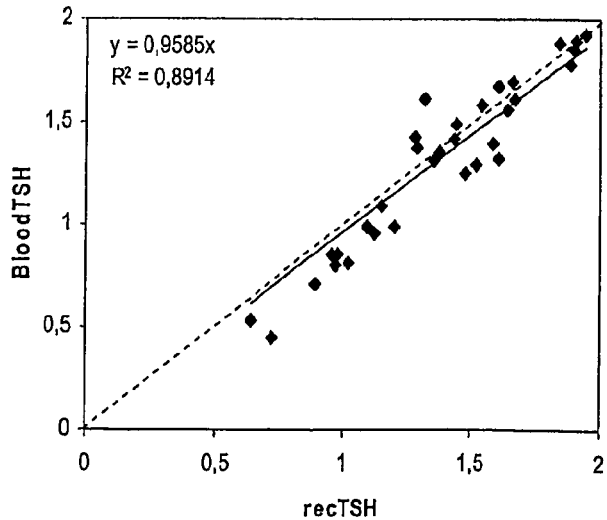

The results are summed up in FIGS. 20A-20C. It clearly appears from FIG. 20C that recTSH presents an antibody binding profile close to that of plasma TSH. Thus, under the experimental conditions described herein, recTSH should prove a better TSH immunologic assays calibrant than the currently used pitTSH.

However, an even better calibrant than recTSH should be provided for clinical assays, since such assays are performed rapidly, i.e. before equilibrium is reached. Thus, preliminary results by the inventors indicate that several glycoforms of recTSH have enhanced antibody binding properties as compared to recTSH itself. Such glycoforms notably encompass oversialylated or resialylated glycoforms of recTSH and/or defucosylated glycoforms of recTSH.

Furthermore, the following formats seem most adapted for plasma TSH assays: Ia/Ib, Ia/II, Ib/II, Ia/III, Ib/III and III/II.

REFERENCES

Spencer, C. A., Takeuchi, M., Kazarosyan, M., MacKenzie, F., Beckett, G. J., and Wilkinson, E. (1995) Interlaboratory/intermethods differences in functional sensitivity of immunometric assays of thyrotropin (TSH) and impact on variability of measurements of subnormal concentrations of TSH. *Clin. Chem.* 41 (3): 367-374.

Spencer, C. A., and Demers, L. M. (2003) Laboratory medicine practice guidelines: Laboratory support for the diagnosis and monitoring of thyroid disease. *Clin. Endocrinol. (Oxf).* 58 (2): 138-140.

Zerfaoui, M. and Ronin, C. (1996) Glycosylation is the structural basis for changes in polymorphism and immunoreactivity of pituitary glycoprotein hormones. *Eur. J. Clin. Chem. Clin. Biochem.* 34:749-753.

Methods on Glycoconjugates: a laboratory manual (1995) Ed: André Verbert, Harwood Academic Publishers.

Benkirane, M. M., Bon, D., Costagliola, S., Paolucci, F., Darbouret, B., Prince, P., and Carayon, P. (1987) Monoclonal antibody mapping of the antigenic surface of human thyrotropin and its subunits. *Endocrinology.* 121 (3): 1171-1177.

Grossmann, M., Szkudlinski, M. W., Tropea, J. E., Bishop, L. A., Thotakura, N. R., Schofield, P. R., and Weintraub, B. D. (1995) Expression of human thyrotropin in cell lines with different glycosylation patterns combined with mutagenesis of specific glycosylation sites. Characterization of a novel role for the oligosaccharides in the in vitro and in vivo bioactivity. *J. Biol. Chem.* 270 (49): 29378-29385.

Canonne, C., Papandreou, M-J., Medri, G., Verrier, B., and Ronin, C. (1995) Biological and immunochemical characterization of recombinant human thyrotropin. *Glycobiology.* 5 (5): 473-481.

Papandreou, M-J., Persani, L., Asteria, C., Ronin, C. and Beck-Peccoz, P. (1993) Variable carbohydrate structures of circulating thyrotropin as studied by lectin affinity chromatography in different clinical conditions. *J. Clin. Endocrinol. Metab.* 77 (2): 393-398.

Gervais, A., Hammel, Y. A., Pelloux, S., Lepage, P., Baer, G., Carte, N., Sorokine, O., Strub, J. M., Koerner, R., Leize, E., and Van Dorsselaer, A. (2003) Glycosylation of human recombinant gonadotrophins: characterization and batch-to-batch consistency. *Glycobiology.* 13 (3): 179-189.

Kashiwai, T., Ichihara, K., Endo, Y., Tamaki, H., Amino, N., and Miyai, K. (1991) Immunological and biological characteristics of recombinant human thyrotropin. *J. Immunol. Methods.* 143: 25-30.

Legaigneur, P., Breton, C., El Battari, A., Guillemot, J-C., Auge, C., Malissard, M., Berger, E. G., and Ronin, C. (2001) Exploring the acceptor substrate recognition of the human beta-galactoside alpha 2,6-sialyltransferase. *J. Biol. Chem.* 276 (24): 21608-21617.

Szkudlinski, M. W., Thotakura, N. R., Tropea, J. E., Grossmann, M., and Weintraub, B. D. (1995) Asparagine-linked oligosaccharide structures determine clearance and organ distribution of pituitary and recombinant thyrotropin. *Endocrinology.* 136 (8): 3325-3330.

Kohler, G., and Milstein, C. (1975) Continuous cultures of fused-cells secreting antibody of predefined specificity. *Nature*. 256: 495-497.

Price A, Burgin C, Catch I, and Cruise M. Functional sensitivity and recovery of thyroid-stimulating hormone. Clin Chem. 2001; 47(11): 2067.

Rafferty B and Gaines Das R. Comparison of pituitary and recombinant human Thyroid-Stimulating Hormone (rhTSH) in a multicenter collaborative study: establishment of the first World Health Organization Reference Reagent for rhTSH. Clin Chem 1999; 45(12): 2207-2215.

Miura Y, Perkel V S, Papenberg K A, Johnson M J, and Magner J A. Concanavalin-A, lentil, and ricin lectin affinity binding characteristics of human thyrotropin: differences in the sialylation of thyrotropin in sera of euthyroid, primary, and central hypothyroid patients. J Clin Endocrinol Metab 1989; 69(5): 985-995.

Unverzagt C, Andre S, Seifert J, Kojima S, Fink C, Srikrishna G, Freeze H, Kayser K, and Gabius H J. Structure-activity profiles of complex biantennary glycans with core fucosylation and with/without additional alpha 2,3/alpha 2,6 sialylation: synthesis of neoglycoproteins and their properties in lectin assays, cell binding, and organ uptake. J Med Chem 2002; 45(2): 478-491.

Schaaf L, Trojan J, Helton T E, Usadel K H, and Magner J A. Serum thyrotropin (TSH) heterogeneity in euthyroid subjects and patients with subclinical hypothyroidism: the core fucose content of TSH-releasing hormone-released TSH is altered, but not the net charge of TSH. J Endocrinol. 1995; 144(3): 561-571.

---

The invention claimed is:

1. A process for screening glycoform specific antibodies capable of binding to at least one given glycoform of a second glycoprotein among antibodies elicited against a first glycoprotein,
   said first glycoprotein being pituitary or blood human TSH from healthy subjects,
   said second glycoprotein being a recombinant human TSH produced by mammalian cells and said second glycoprotein being itself a glycoform of the first glycoprotein,
   said process comprising the following steps:
   checking that a panel of antibodies elicited against the first glycoprotein bind to said recombinant human TSH, said antibodies being classified in pools, each pool being characterized in that two antibodies selected from the same pool can not bind to the same glycoprotein at the same time,
   (1) contacting said panel of antibodies elicited against the first glycoprotein with at least one glycoform of said recombinant human TSH,
   (2) determining the binding affinity between said antibodies and the first glycoprotein, or said recombinant human TSH, or at least one glycoform of said recombinant human TSH, and
   recovering antibodies recognizing said recombinant human TSH, or at least one glycoform of said recombinant human TSH with a higher affinity than that displayed with the first glycoprotein,
   wherein said glycoform of said recombinant human TSH is selected from a group of glycoforms of said recombinant human TSH, each glycoform of said group corresponding to a determined glycosylation state being:
   a) essentially more sialylated, more branched and less fucosylated than the recombinant human TSH, or
   b) essentially more sialylated, less branched and less fucosylated than the recombinant human TSH.

2. The process according to claim 1, wherein a glycoform of said recombinant human TSH is:
   a) essentially more sialylated, more branched and less fucosylated than the recombinant human TSH, or
   b) essentially more sialylated, less branched and less fucosylated than the recombinant human TSH, and
   is obtained by a combination
   of at least one enzymatic modification of recombinant human TSH, and/or
   of at least one lectin fractionation.

3. The process according to claim 2, wherein the at least one lectin fractionation is carried out by a lectin selected from the group consisting of a mannose-specific lectin, a fucose-specific lectin, a gactose-specific lectin, and a sialic acid-specific lectin.

4. The process according to claim 2, wherein the enzymatic modification is carried out by an enzyme selected from the group consisting of
   a glycosidase, and
   a glycosyltransferase.

5. The process according to claim 4, wherein
   the glycosidase is a neuraminidase or a fucosidase, and wherein
   the glycosyltransferase is a sialyltransferase.

6. The process according to claim 2, wherein said less fucosylated glycoform of recombinant TSH is obtained by lentil fractionation and collecting the fraction which does not bind to lentil.

7. The process according to claim 2, wherein the more sialylated glycoform of said recombinant human TSH is obtained by sialyltransferase treatment.

8. The process according to claim 7, wherein the sialyltransferase is a α-2,6-sialyltransferase having an increased solubility and a superior activity.

9. The process according to claim 8, wherein said α-2,6-sialyltransferase is a N-terminally shortened ST6Gal I sialyltransferase having its first 99 residues as set forth in SEQ ID NO: 1.

10. The process according to claim 1, wherein the binding of the antibodies to the first glycoprotein, or to the recombinant TSH or to the glycoforms of the recombinant TSH is determined by immunoassays.

11. The process according to claim 10, wherein the immunoassays are immunoassay formats comprising an amplification system for detection.

12. The process according to claim 10 or 11, wherein the immunoassays are sandwich immunoassays, comprising the following steps:
   fixing a capture antibody selected from a pool onto a solid phase, each pool being characterized in that two antibodies selected from the same pool can not bind to the same glycoprotein at the same time,
   contacting a glycoprotein, corresponding to the first glycoprotein, or to the recombinant TSH or a glycoforms of the recombinant TSH, to said capture antibody, to form a capture antibody-glycoprotein binary complex,
   contacting a tracer antibody, selected from a pool, each pool being characterized in that two antibodies selected from the same pool cannot bind to the same glycoprotein at the same time, provided said pool is different from the one used for the selection of said capture antibody, to said capture antibody-glycoprotein binary complex, to form a capture antibody-glycoprotein-tracer antibody ternary complex,
   detecting the tracer antibody for measuring the number of ternary complexes.

13. The process according to claim 3, wherein the lectin is selected from the group consisting of a ConA lectin, a Lentil lectin, an Ulex lectin, a ricin, a limulin lectin and a *Sambucus nigra* lectin.

14. The process according to claim 11, wherein the immunoassays are an ELISA format.

15. The process according to claim 3, wherein the manose-specific lectin is ConA.

16. The process according to claim 15, wherein a ConA fractionation of said recombinant human TSH is performed by collecting three fractions, A, B, and C, the binding of which to ConA is such that, fraction C binds to ConA more strongly than fraction B binds to ConA, and fraction B binds to ConA more strongly than fraction A binds to ConA, the branching state of a given fraction being essentially different from the branching state of the other two fractions.

* * * * *

SEQUENCE LISTING

```
<160> NUMBER OF SEQ ID NOS: 1

<210> SEQ ID NO 1
<211> LENGTH: 317
<212> TYPE: PRT
<213> ORGANISM: Artificial sequence
<220> FEATURE:
<223> OTHER INFORMATION: 1-89 deletion mutant of human ST6GalI

<400> SEQUENCE: 1

Glu Ala Ser Phe Gln Val Trp Asn Lys Asp Ser Ser Lys Asn Leu
1               5                   10                  15

Ile Pro Arg Leu Gln Lys Ile Trp Lys Asn Tyr Leu Ser Met Asn Lys
            20                  25                  30

Tyr Lys Val Ser Tyr Lys Gly Pro Gly Pro Gly Ile Lys Phe Ser Ala
            35                  40                  45

Glu Ala Leu Arg Cys His Leu Arg Asp His Val Asn Val Ser Met Val
    50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
                85                  90                  95

Val Val Ser Ser Ala Gly Ser Leu Lys Ser Ser Gln Leu Gly Arg Glu
                100                 105                 110

Ile Asp Asp His Asp Ala Val Leu Arg Phe Asn Gly Ala Pro Thr Ala
            115                 120                 125

Asn Phe Gln Gln Asp Val Gly Thr Lys Thr Thr Ile Arg Leu Met Asn
        130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
                165                 170                 175

Ile Pro Lys Trp Tyr Gln Asn Pro Asp Tyr Asn Phe Phe Asn Asn Tyr
            180                 185                 190

Lys Thr Tyr Arg Lys Leu His Pro Asn Gln Pro Phe Tyr Ile Leu Lys
        195                 200                 205

Pro Gln Met Pro Trp Glu Leu Trp Asp Ile Leu Gln Glu Ile Ser Pro
    210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
```

-continued

```
                    245                 250                 255
Ser Lys Arg Lys Thr Asp Val Cys Tyr Tyr Gln Lys Phe Phe Asp
            260                 265                 270

Ser Ala Cys Thr Met Gly Ala Tyr His Pro Leu Leu Tyr Glu Lys Asn
        275                 280                 285

Leu Val Lys His Leu Asn Gln Gly Thr Asp Glu Asp Ile Tyr Leu Leu
        290                 295                 300

Gly Lys Ala Thr Leu Pro Gly Phe Arg Thr Ile His Cys
305                 310                 315
```